(12) United States Patent
Shao et al.

(10) Patent No.: US 12,196,728 B2
(45) Date of Patent: Jan. 14, 2025

(54) SYSTEMS AND METHODS FOR MEASURING ENERGY OF NATURAL GAS COMPONENTS

(71) Applicant: CHENGDU QINCHUAN IOT TECHNOLOGY CO., LTD., Sichuan (CN)

(72) Inventors: Zehua Shao, Chengdu (CN); Haitang Xiang, Chengdu (CN); Yaqiang Quan, Chengdu (CN); Bin Liu, Chengdu (CN)

(73) Assignee: CHENGDU QINCHUAN IOT TECHNOLOGY CO., LTD., Chengdu (CN)

( * ) Notice: Subject to any disclaimer, the term of this patent is extended or adjusted under 35 U.S.C. 154(b) by 406 days.

(21) Appl. No.: 17/649,344

(22) Filed: Jan. 28, 2022

(65) Prior Publication Data
US 2022/0163498 A1 May 26, 2022

(30) Foreign Application Priority Data

Feb. 4, 2021 (CN) .................... 202110154157.X
Jan. 14, 2022 (CN) .................... 202210045110.4

(51) Int. Cl.
*G01N 33/36* (2006.01)
*G01N 33/00* (2006.01)
(Continued)

(52) U.S. Cl.
CPC ......... *G01N 33/0036* (2013.01); *G16C 20/30* (2019.02); *G16C 20/70* (2019.02); *G06F 2113/14* (2020.01)

(58) Field of Classification Search
CPC ........... G01N 33/0004; G01N 33/0036; G01N 33/0067; G01N 2033/0068;
(Continued)

(56) References Cited

U.S. PATENT DOCUMENTS 6,612,186 B1* 9/2003 Patten .................. G01N 33/225
73/861.04
2004/0030520 A1* 2/2004 Matter .................. G01F 15/046
702/45
(Continued)

FOREIGN PATENT DOCUMENTS

CA 1325343 C 12/1993
CN 1731147 A 2/2006
(Continued)

OTHER PUBLICATIONS

Su, Meng et al., Application of Edge Detection in Flame Photos Processing for Natural Gas Fuel, Design & Manufacture of Diesel Engine, 19(4): 16-19+31, 2013.
(Continued)

*Primary Examiner* — Son T Le
*Assistant Examiner* — Matthew W. Baca
(74) *Attorney, Agent, or Firm* — METIS IP LLC

(57) ABSTRACT

The disclosure provides a method for measuring energy of natural gas components. The method may comprise obtaining, at a plurality of time points, the natural gas components at a target position in a natural gas transmission channel to obtain a distribution of the natural gas components in an area that the natural gas energy is to be measured. The method may comprise determining, based on the calorific value of natural gas at the each time point in each subarea of the plurality of subareas, a calorific value distribution function corresponding to the each subarea. The method may comprise determining, based on the calorific value distribution function corresponding to the each subarea, natural gas energy of the each subarea. The method may comprise determining, based on the natural gas energy of the each subarea, the natural gas energy of the area that the natural gas energy is to be measured.

13 Claims, 9 Drawing Sheets

(51) Int. Cl.
*G16C 20/30* (2019.01)
*G16C 20/70* (2019.01)
*G06F 113/14* (2020.01)

(58) Field of Classification Search
CPC ............ G01N 33/1846; G01N 33/225; G01N 33/241; G01N 33/2835; G01N 2030/025; G01N 2030/027; G16C 20/20; G16C 20/30; G16C 20/70; G06F 2113/14; G01R 21/1276; F23N 2221/10; F17C 2250/0456; F17C 2250/0652; F23G 2201/601

See application file for complete search history.

(56) References Cited

U.S. PATENT DOCUMENTS

| | | |
|---|---|---|
| 2011/0164039 A1 | 7/2011 | Anklam et al. |
| 2013/0113939 A1 | 5/2013 | Strandemar |
| 2013/0152665 A1 | 6/2013 | Dunlop et al. |
| 2018/0173839 A1 | 6/2018 | Fang et al. |
| 2021/0135454 A1 | 5/2021 | Harbaugh et al. |
| 2023/0394453 A1* | 12/2023 | Ding .................... G06Q 20/145 |

FOREIGN PATENT DOCUMENTS

| | | |
|---|---|---|
| CN | 101038252 A | 9/2007 |
| CN | 101131353 A | 2/2008 |
| CN | 205593617 U | 9/2016 |
| CN | 107274568 A | 10/2017 |
| CN | 107451590 A | 12/2017 |
| CN | 107941276 A | 4/2018 |
| CN | 109852748 A | 6/2019 |
| CN | 109995964 A | 7/2019 |
| CN | 111060479 A | 4/2020 |
| CN | 111161293 A | 5/2020 |
| CN | 210923595 U | 7/2020 |
| CN | 111486930 A | 8/2020 |
| CN | 112150371 A | 12/2020 |
| CN | 112836178 A | 5/2021 |
| CN | 113189952 A | 7/2021 |
| CN | 113344801 A | 9/2021 |
| CN | 113884985 A | 1/2022 |
| CN | 114400056 A | 4/2022 |
| WO | 2018231735 A1 | 12/2018 |

OTHER PUBLICATIONS

Bao, Min, Research on the Main Factors Causing Error on Measurement of Ultrasonic Gas Flowmeters: Theory and Applications, Chinese Selected Doctoral Dissertations and Master's Theses Full-Text Databases, 2004, 125 pages.

Bhargav Shah et al., Tsallis Entropic thresholding based segmentation of Gas Puff Images of Plasma Using Normalize Grey Level Spatial Correlation Histogram, 2020 International Conference on Artificial Intelligence and Signal Processing, 2020, 6 pages.

Chen, Ching-Han et al., Efficient Vision-based Smart Meter Reading Network, International Journal of Web Services Research, 14(1): 44-58, 2017.

Shao, Zehua et al., Electricity Self-supply Device of IoT Intelligent Gas Meter, Gas & Heat, 2021, 4 pages.

Qiu, Zhi, Research on Natural Gas Energy Measurement Method, Wanfang Theses Database, 2006, 82 pages.

First Office Action in Chinese Application No. 202110154157.X mailed on Jan. 17, 2022, 13 pages.

Zhao, Mingbin et al., Safety Analysis of Hydrogen Fuel Cell Vehicle Leakage and Explosion Accident in An Underground Parking Garage, Full-text Database of China's Excellent Master's Thesis, Engineering Science and Technology Series I, 2021, 116 pages.

Behzad Zargar et al., Multiarea Parallel Data-driven Three-Phase Distribution System State Estimation Using Synchrophasor Measurements, IEEE Transactions on Instrumentation and Measurement, 69(9): 6186-6202, 2020.

* cited by examiner

200

```
┌─────────────────────────────────────────────────────┐
│ Obtaining, at each of a plurality of time points,    │  202
│ natural gas components at a target position in a     │
│ natural gas transmission channel to obtain a         │
│ distribution of the natural gas components in an     │
│ area that the natural gas energy is to be measured   │
└─────────────────────────────────────────────────────┘
                          ↓
┌─────────────────────────────────────────────────────┐
│ Determining, based on the natural gas of the         │  204
│ distribution of the natural gas components at the    │
│ each time point, a calorific value of natural gas    │
│ at the each time point                               │
└─────────────────────────────────────────────────────┘
                          ↓
┌─────────────────────────────────────────────────────┐
│ Determining a direction cosine value of the          │  206
│ calorific value of the natural gas at the each       │
│ time point                                           │
└─────────────────────────────────────────────────────┘
                          ↓
┌─────────────────────────────────────────────────────┐
│ Determining a variable quantity of the direction     │
│ cosine value at the each time point, and             │  208
│ determining, based on the variable quantity, at      │
│ least one time point as at least one cutpoint, the   │
│ at least one cutpoint being configured to determine  │
│ a plurality of subareas of the area that the         │
│ natural gas energy is to be measured                 │
└─────────────────────────────────────────────────────┘
                          ↓
┌─────────────────────────────────────────────────────┐
│ Determining, based on the calorific value of the     │  210
│ natural gas at the each time point in each subarea   │
│ of the plurality of subareas, a calorific value      │
│ distribution function corresponding to the each      │
│ subarea                                              │
└─────────────────────────────────────────────────────┘
                          ↓
┌─────────────────────────────────────────────────────┐
│ Determining, based on the calorific value            │  212
│ distribution function corresponding to the each      │
│ subarea, natural gas energy of the each subarea of   │
│ the plurality of subareas                            │
└─────────────────────────────────────────────────────┘
                          ↓
┌─────────────────────────────────────────────────────┐
│ Determining, based on the natural gas energy of      │  214
│ the each subarea of the plurality of subareas, the   │
│ natural gas energy of the area that the natural      │
│ gas energy is to be measured                         │
└─────────────────────────────────────────────────────┘
```

SYSTEMS AND METHODS FOR MEASURING ENERGY OF NATURAL GAS COMPONENTS

CROSS REFERENCE TO RELATED APPLICATIONS

This application claims priority of Chinese Patent Application No. 202110154157.X, filed on Feb. 4, 2021, and priority of Chinese Patent Application No. 202210045110.4, filed on Jan. 14, 2022, the entire contents of which are incorporated herein by reference.

TECHNICAL FIELD

The present disclosure relates to the field of data processing, and in particular, to systems and methods for measuring energy of natural gas components.

BACKGROUND

Natural gas is mixture gas composed of various flammable and non-flammable gases. In a process of transferring and measuring large-scale natural gas, due to the differences in the natural gas components at different places, the fluctuation of natural gas component data at the same position and at different times, a natural gas transportation pipeline that does not satisfy standards, or the like, there are differences in a calorific value of natural gas, which causes that a volume measurement manner of natural gas is not able to accurately measure the actual consumption of the combustible gas in the natural gas, and the measurement and charging are unreasonable and unfair.

Therefore, it is desirable to provide a manner for measuring natural gas based on energy measurement, which may perform a precise energy measurement for the natural gas composed of different components to achieve a reasonable measurement.

SUMMARY

One aspect of the embodiments of the present disclosure provides a method for measuring energy of natural gas components. The method may comprise obtaining, at each of a plurality of time points, the natural gas components at a target position in a natural gas transmission channel to obtain a distribution of the natural gas components in an area that the natural gas energy is to be measured. The method may also comprise determining, based on the natural gas components of the distribution of the natural gas components at the each time point, a calorific value of the natural gas at the each time point. The method may also comprise determining a direction cosine value of the calorific value of the natural gas at the each time point, determining a variable quantity of the direction cosine value at the each time point, and determining, based on the variable quantity, at least one time point as at least one cutpoint, the at least one cutpoint being configured to determine a plurality of subareas of the area that the natural gas energy is to be measured. The method may also comprise determining, based on the calorific value of the natural gas at the each time point in each subarea of the plurality of subareas, a calorific value distribution function corresponding to the each subarea. The method may also comprise determining, based on the calorific value distribution function corresponding to the each subarea, natural gas energy of the each subarea of the plurality of subareas. The method may also comprise determining, based on the natural gas energy of the each subarea of the plurality of subareas, the natural gas energy of the area that the natural gas energy is to be measured.

In some embodiments, determining, based on the calorific value of the natural gas at the each time point in each subarea of the plurality of subareas, a calorific value distribution function corresponding to the each subarea, may include for each of the plurality of subareas, determining, based on a calorific value of the natural gas corresponding to a first time point and a calorific value of the natural gas corresponding to a last time point in the subarea, a linear function as the calorific value distribution function of the natural gas corresponding to the each subarea.

In some embodiments, determining, based on the calorific value of the natural gas at the each time point in each subarea of the plurality of subareas, a calorific value distribution function corresponding to the each subarea may include for each subarea of the plurality of subareas, obtaining a fitting function based on a curve-fitting manner that is configured to fit the calorific value of the natural gas at the each time point in the subarea, and designating the fitting function as the calorific value distribution function corresponding to the each subarea.

In some embodiments, determining, based on the calorific value of the natural gas at the each time point in each subarea of the plurality of subareas, a calorific value distribution function corresponding to the each subarea may include for each of the plurality of subareas, obtaining a temperature and a flow rate of the natural gas at the each time point in the subarea, and determining, based on a first prediction model that is configured to process the calorific value of the natural gas, the temperature, and the flow rate of the natural gas at the each time point in the subarea, the calorific value distribution function corresponding to the each subarea.

In some embodiments, the method may further include obtaining, based on the natural gas components at the each time point in the distribution of the natural gas components, a distribution of natural gas components in the each subarea, and determining, based on the distribution of natural gas components in the each subarea, a decontamination manner of the natural gas corresponding to the each subarea, wherein the decontamination manner of the natural gas corresponding to a subarea may be configured to perform the decontamination on the natural gas in the subarea. The method may also include determining, based on the calorific value distribution function corresponding to the each subarea and the decontamination manner of the natural gas, a calorific value distribution function of the natural gas corresponding to the each subarea after performing the decontamination manner, and determining, based on the calorific value distribution function of the natural gas after performing the decontamination manner, the natural gas energy of the each subarea of the plurality of subareas.

In some embodiments, determining, based on the distribution of the natural gas components in the each subarea, a decontamination manner of the natural gas corresponding to the each subarea may include determining, based on the distribution of the natural gas components in the each subarea, a component variation range of combustible gas or impurities of the each subarea, and determining, based on the component variation range of the combustible gas or the impurities of the each subarea, the decontamination manner of the natural gas corresponding to the each subarea.

In some embodiments, determining, based on the calorific value distribution function of the natural gas corresponding to the each subarea and the decontamination manner of the natural gas, a distribution function of the calorific value of the natural gas corresponding to the each subarea after performing the decontamination manner may include determining, based on the decontamination manner of the natural gas corresponding to the each subarea, a second prediction model corresponding to the each subarea, and obtaining, based on the second prediction model that is configured to process the calorific value distribution function of the natural gas corresponding to the each subarea, the calorific value distribution function of the natural gas corresponding to the each subarea after performing the decontamination manner.

Another aspect of the embodiments of the present disclosure provides a system for measuring energy of natural gas components. The system may comprise at least one storage device including a set of instructions, and at least one processor in communication with the at least one storage device, wherein when executing the set of instructions, the at least one processor is configured to cause the system to perform at least one operation, comprising: obtaining, at each of a plurality of time points, the natural gas components at a target position in a natural gas transmission channel to obtain a distribution of the natural gas components in an area that the natural gas energy is to be measured. The system may also comprise determining, based on the natural gas components of the distribution of the natural gas components at the each time point, a calorific value of the natural gas at the each time point. The system may also comprise determining a direction cosine value of the calorific value of the natural gas at the each time point, determining a variable quantity of the direction cosine value at the each time point, and determining, based on the variable quantity, at least one time point as at least one cutpoint, the at least one cutpoint being configured to determine a plurality of subareas of the area that the natural gas energy is to be measured. The system may also comprise determining, based on the calorific value of the natural gas at the each time point in each subarea of the plurality of subareas, a calorific value distribution function corresponding to the each subarea. The system may also comprise determining, based on the calorific value distribution function corresponding to the each subarea, natural gas energy of the each subarea of the plurality of subareas, and determining, based on the natural gas energy of the each subarea of the plurality of subareas, the natural gas energy of the area that the natural gas energy is to be measured.

A non-transitory computer readable medium storing instructions, when executed by at least one processor, causing the at least one processor to implement a method, and the method may comprise obtaining, at each of a plurality of time points, the natural gas components at a target position in a natural gas transmission channel to obtain a distribution of the natural gas components in an area that the natural gas energy is to be measured. The method may also comprise determining, based on the natural gas components of the distribution of the natural gas components at the each time point, a calorific value of the natural gas at the each time point. The method may also comprise determining a direction cosine value of the calorific value of the natural gas at the each time point, determining a variable quantity of the direction cosine value at the each time point, and determining, based on the variable quantity, at least one time point as at least one cutpoint, the at least one cutpoint being configured to determine a plurality of subareas of the area that the natural gas energy is to be measured. The method may also comprise determining, based on the calorific value of the natural gas at the each time point in each subarea of the plurality of subareas, a calorific value distribution function corresponding to the each subarea. The method may also comprise determining, based on the calorific value distribution function corresponding to the each subarea, natural gas energy of the each subarea of the plurality of subareas. The method may also comprise determining, based on the natural gas energy of the each subarea of the plurality of subareas, the natural gas energy of the area that the natural gas energy is to be measured.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 2 is an exemplary flowchart of a method for measuring natural gas energy according to some embodiments of the present disclosure;

DETAILED DESCRIPTION

Figure 1:
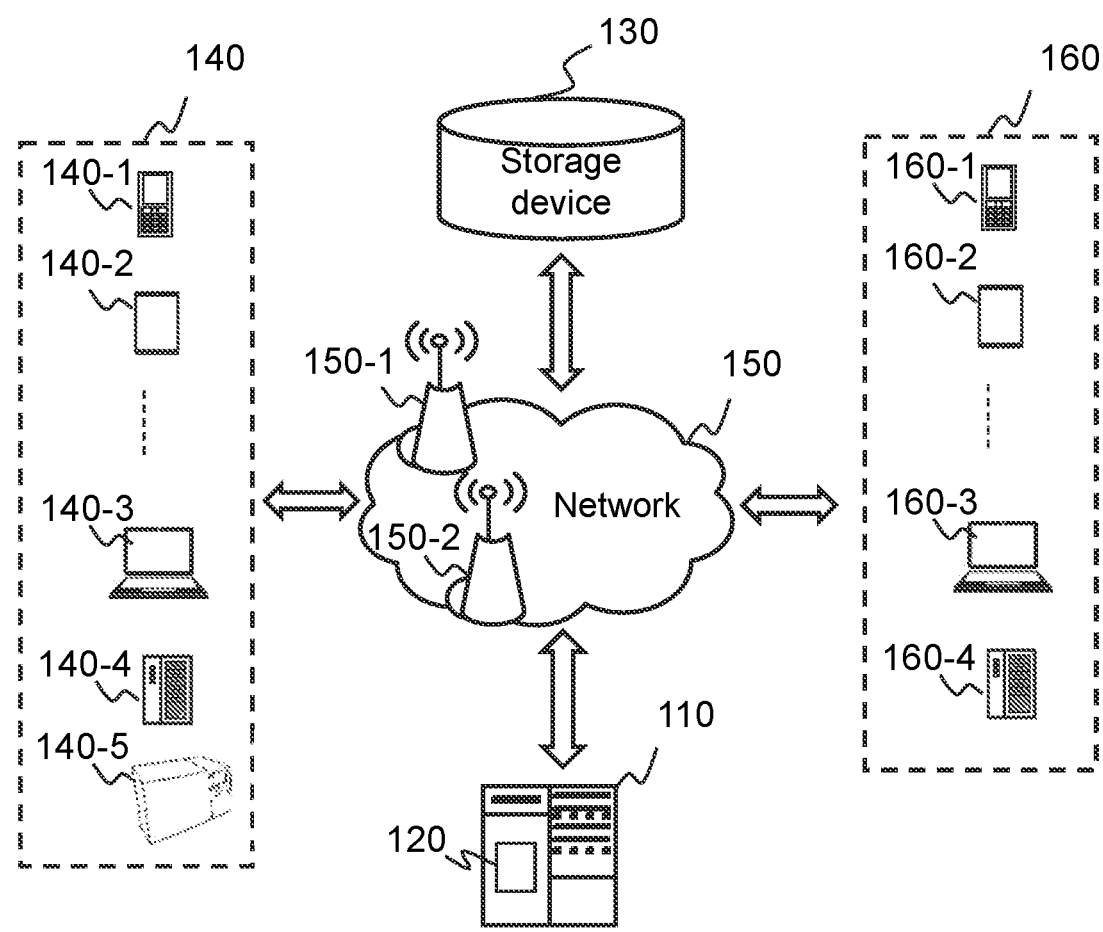
FIG. 1 is a schematic diagram illustrating an application scenario of a system for measuring natural gas energy according to some embodiments of the present disclosure.

In the following detailed description, numerous specific details are set forth by way of examples in order to provide a thorough understanding of the relevant disclosure. Obviously, drawings described below are only some examples or embodiments of the present disclosure. Those skilled in the art, without further creative efforts, may apply the present disclosure to other similar scenarios according to these drawings. Unless obviously obtained from the context or the context illustrates otherwise, the same numeral in the drawings refers to the same structure or operation.

It will be understood that the term "system," "engine," "unit," "module," and/or "block" used herein are one method to distinguish different components, elements, parts, sections, or assembly of different levels in ascending order.

However, the terms may be displaced by another expression if they achieve the same purpose.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

The flowcharts used in the present disclosure illustrate operations that systems implement according to some embodiments of the present disclosure. It is to be expressly understood the operations of the flowcharts may be implemented not in order. Conversely, the operations may be implemented in an inverted order, or simultaneously. Moreover, one or more other operations may be added to the flowcharts. One or more operations may be removed from the flowcharts.

The embodiments of the present disclosure provide a method, system, and storage medium for measuring energy of natural gas components. The method for measuring natural gas energy may be applied to smart terminals such as a mobile phone, a tablet computer, a notebook computer, or the like, and the application fields may be energy measurement, chemical research, or the like. In some embodiments, the method, system, and storage medium for measuring natural gas energy may be applied to a measurement terminal that is used to measure a distribution of the natural gas components, for example, a monitor for all natural gas components, a gas chromatograph, or the like. In some embodiments, the method, system, and storage medium for measuring natural gas energy may be applied to a management or user terminal, for example, a monitoring platform of natural gas components, or the like.

FIG. 1 is a schematic diagram illustrating an application scenario of a system for measuring natural gas energy according to some embodiments of the present disclosure.

The application scenario may include a server 110, a storage device 130, a first terminal 140, a network 150, and a second terminal 160.

A system 100 for measuring natural gas energy may be used in scenarios involving a service platform of natural gas measurement. In some embodiments, the system may be used in an oil and gas gathering and transporting system, an oil and gas control center, a natural gas supply station, a gas storage and distribution station, or the like. The system 100 for measuring natural gas energy may realize the measurement of natural gas energy by performing methods and/or processes disclosed in some embodiments of the present disclosure.

In some embodiments, the server 110 may be used to process information and/or data related to the system 100 for measuring natural gas energy. For example, a calorific value of the natural gas at each time point may be determined based on the natural gas components at the each time point in the distribution of the natural gas components. In some embodiments, the server 110 may be a single server or a server group. The server group may be a centralized server group or a distributed server group (e.g., the server 110 may be a distributed system). In some embodiments, the server 110 may be a local server or a remote server. For example, the server 110 may access information and/or data stored in the storage device 130, the first terminal 140, and the second terminal 160 via the network 150. As another example, the server 110 may be directly connected to the storage device 130, the first terminal 140, and/or the second terminal 160 to access stored information and/or data.

In some embodiments, the server 110 may include a processing device 120. The processing device 120 may process information and/or data related to the system 100 for measuring natural gas energy to perform one or more functions described in the present disclosure. For example, the processing device 120 may determine a calorific value of the natural gas at each time point based on the natural gas components at the each time point in the distribution of the natural gas components. In some embodiments, the processing device 120 may include one or more processing engines (e.g., a single-chip processing engine or a multi-chip processing engine). Merely as an example, the processing device 120 may include a central processing unit (CPU).

The storage device 130 may be used to store data and/or instructions related to the measurement of the natural gas energy. In some embodiments, the storage device 130 may store data obtained or acquired from the first terminal 140 and/or the second terminal 160. In some embodiments, the storage device 130 may store data and/or instructions used by the server 110 to perform or achieve the exemplary methods described in the present disclosure. In some embodiments, the storage device 130 may be implemented on a cloud platform. In some embodiments, the storage device 130 may be connected to the network 150 to communicate with one or more components (e.g., the server 110, the first terminal 140, the second terminal 160) of the system 100 for measuring natural gas energy. The one or more components of the system 100 for measuring natural gas energy may access data or instructions stored in the storage device 130 via the network 150. In some embodiments, the storage device 130 may be directly connected to or in communication with the one or more components (e.g., the server 110, the first terminal 140, the second terminal 160) of the system 100 for measuring natural gas energy. In some embodiments, the storage device 130 may be part of the server 110. In some embodiments, the storage device 130 may be a separate storage device.

The first terminal 140 may be a device or other entity directly related to the acquisition of the natural gas components. In some embodiments, the first terminal 140 may be an operator obtaining distribution data of the natural gas components. In some embodiments, the first terminal 140 may include a mobile device 140-1, a tablet computer 140-2, a notepad 140-3, a laptop 140-4, an analytical device 140-5, or the like, or any combination thereof. In some embodiments, the mobile terminal 140-1 may include a smartphone, a smart paging device, or the like, or other smart devices. In some embodiments, the analysis device 140-5 may include a monitor for all components, a gas chromatograph, or the like. In some embodiments, the first terminal 140 may include other smart terminals, such as wearable smart terminals, or the like. The first terminal 140 may be a smart terminal or an entity including a smart terminal, such as a pipeline including an analysis device, or the like.

The network 150 may facilitate the exchange of information and/or data. In some embodiments, one or more components of the system 100 for measuring natural gas energy (e.g., the server 110, the first terminal 140, the second terminal 160) may transmit information and/or data to other components of the system 100 for measuring natural gas energy via the network 150. For example, the server 110 may obtain the distribution data of the natural gas components from the first terminal 140 via the network 150. In some embodiments, the network 150 may be a wired network, a wireless network, or the like, or any combination thereof. Merely as an example, the network 150 may include a cable network. In some embodiments, the system 100 for measuring natural gas energy may include one or more network access points, for example, base stations and/or wireless access points 150-1, 150-2, . . . . One or more components of the system 100 for measuring natural gas energy may be connected to the network 150 to exchange data and/or information.

The second terminal 160 may be a terminal used by the user, for example, the terminal used by an experimenter, or the like. In some embodiments, the second terminal 160 may be a requester requesting to obtain the distribution data of the natural gas components. In some embodiments, "role", "user", and "user terminal" may be used interchangeably. In some embodiments, the user may be an operator or user of the system 100 for measuring natural gas energy, for example, a member performing a measurement, a researcher, or the like. In some embodiments, the second terminal 160 may include a mobile device 160-1, a tablet computer 160-2, a notepad 160-3, a laptop computer 160-4, or the like, or any combination thereof. In some embodiments, the second terminal 160 may receive the information uploaded by the first terminal 140 via the network 150, such as the distribution data of the natural gas components, or the like.

It should be noted that the system 100 for measuring natural gas energy is provided merely for illustration purposes, which is not intended to limit the scope of the present disclosure. For those skilled in the art, various modifications or changes may be made based on the description of the present disclosure. For example, the system 100 for measuring natural gas energy may also include information source. As another example, the system 100 for measuring natural gas energy may implement similar or different functions on other devices. However, such changes and modifications may not depart from the scope of the present disclosure.

FIG. 2 is an exemplary flowchart of a method for measuring natural gas energy according to some embodiments of the present disclosure. As shown in FIG. 2, a process 200 may include the following operations. In some embodiments, the process 200 may be performed by the processing device 120.

In operation S202, the natural gas components may be obtained at a target position in a natural gas transmission channel at each of a plurality of time points to obtain a distribution of the natural gas components in an area where the natural gas energy is to be measured. In some embodiments, the operation S202 may be performed by an area component distribution acquisition module 601.

A natural gas transmission channel may be any apparatus used to contain, transmit, or store natural gas, for example, a gas pipeline, a gas storage tank, a gas storage warehouse, or other gas storage apparatus. In some embodiments, a target position in a natural gas transmission channel may be a location point, an area, or a cross-sectional area of a channel that the natural gas components are detected in the natural gas transmission channel. For example, in a gas pipeline, the cross-sectional area of the gas pipeline may be used as the target position. In some embodiments, the target position may be determined through user settings, factory settings of the natural gas transmission channel, settings of the first terminal 140, or the like, or a combination thereof.

In some embodiments, the system 100 may request and obtain the natural gas components at each of a plurality of time points. The plurality of time points may be time points preset through a system or manually. The natural gas components may be chemical components of the natural gas. For example, common natural gas components mainly include methane, and also include small amounts of ethane, propane, butane, hydrogen, nitrogen, carbon dioxide, sulfide, or the like. At different time points, there may be differences in the natural gas components flowing through the target position in the natural gas transmission channel.

The area that the natural gas energy is to be measured may be a certain section of the natural gas passing through the transmission channel. The component distribution of the certain section of the natural gas is to be analyzed, and the energy of the certain section of the natural gas is to be measured. In some embodiments, the area that the natural gas energy is to be measured may be a section of the natural gas passing through the target position in a pipeline over a period of time. In some embodiments, a volume of the natural gas in the area that the natural gas is to be measured may be determined based on the time and flow rate of the natural gas passing through the target position. For example, the area that the natural gas is to be measured (a section of the natural gas transported by a pipeline) may be a section of the natural gas passing through point A during a period of time T. During the time period T, an average flow rate of the natural gas at point A may be V, and a flow length X of the section of the natural gas (i.e., the area that the natural gas energy is to be measured) may be obtained through multiplying V by T. Further, a volume of the section of the natural gas (i.e., a volume of the natural gas in the area that the natural gas energy is to be measured) may be obtained by multiplying the flow length X of the natural gas by a cross-sectional area of a pipeline at point A.

In some embodiments, the distribution of the natural gas components in the area that the natural gas energy is to be measured may be expressed as a sequence: {S1, S2, S3, S4, S5, S6, . . . , Sn}, and each element Sn in the sequence may be gas component data at a corresponding time point Tn. In some embodiments, the sequence may also indicate that n points are sampled in an area of length X, and Tn may correspond to a location point Xn within the length X. In some embodiments, the length X may include a plurality of location points, such as the location point, the location point, . . . location. In some embodiments, each location point Xn may correspond to each time point Tn.

In some embodiments, the distribution of the natural gas components in the area that the natural gas energy is to be measured may be obtained through the first terminal 140. For example, the distribution of the natural gas components in the area that the natural gas energy is to be measured may be obtained via a gas chromatography, a monitor for all natural gas components, or through Online Raman Spectroscopy. The system 100 may obtain the distribution of the natural gas components at the each time point in the area that the natural gas energy is to be measured by analyzing the distribution of the natural gas components at the plurality of time points in the area that the natural gas energy is to be measured in the natural gas transmission channel. In some embodiments, the distribution of the natural gas components at the each time point in the area that the natural gas energy is to be measured may include data such as a mole fraction, a volume fraction, a mass fraction, or the like, of each component.

In operation S204, a calorific value of the natural gas at the each time point may be determined based on the natural gas components at the each time point of the distribution of the natural gas components. In some embodiments, the operation S204 may be performed by a calorific value determination module 602.

The calorific value of the natural gas may be the heat released when a unit mass (or volume) of the natural gas is burned, and the calorific value unit may be J/kg or J/m$^3$, MJ/kg or MJ/m$^3$. In some embodiments of the present disclosure, "calorific value", "calorie value", "caloric amount", or the like, may be used interchangeably.

In some embodiments, the calorific value of the natural gas may be obtained by various calorific value calculation manners based on the natural gas components. For example, may be calculated through the following equation:

$$\overline{H}^0(t_1) = \Sum_{j=1}^{N} x_j \overline{H}_j^0(t_1) \quad (1)$$

wherein, $\overline{H}^0(t_1)$ refers to an ideal molar calorific value (high or low) of the natural gas mixture, $x_1$ refers to the mole fraction of component j in the mixture, and $\overline{H}_j^0(t_1)$ refers to an ideal molar calorific value (high or low) of the component j in the mixture.

In some embodiments, a real volume calorific value of the gas when the gas mixture is at combustion temperature $t_1$ and pressure $p_1$, metered temperature $t_2$ and pressure $p_2$, may be calculated by the following equation:

$$\tilde{H}[t_1, V(t_2, p_2)] = \frac{\tilde{H}^0[t_1, V(t_2, p_2)]}{Z_{mix}(t_2, p_2)} \quad (2)$$

wherein, $\tilde{H}[t_1,V(t_2,p_2)]$ refers to a volume calorific value of the natural gas (high or low), $\tilde{H}^0[t_1, V(t_2,p_2)]$ refers to an ideal gas volume calorific value of the natural gas mixture, and $Z_{mix}(t_2,p_2)$ refers to a compression factor under a metrological reference condition.

In some embodiments, the calorific value of the natural gas may also be calculated in various other manners.

In operation S206, a direction cosine value of the calorific value of the natural gas at the each time point may be determined. In some embodiments, the operation S206 may be performed by a direction cosine value determination module 603.

In some embodiments, each time point in the area that the natural gas energy is to be measured may correspond to a direction cosine value. The direction cosine value may be a cosine value corresponding to a vector of a line connecting the calorific values of the natural gas (i.e., a calorific value of the natural gas at a certain point in the flow length of the natural gas of the area that the natural gas energy is to be measured) at various time points in the area that the natural gas energy is to be measured. In some embodiments, the calculation of the direction cosine value of each point may be determined according to the distribution of the calorific value of the natural gas in the area that the natural gas energy is to be measured (including the calorific value of the natural gas corresponding to the gas components at each location point in the flow length of the natural gas corresponding to the area that the natural gas energy is to be measured). For example, the cosine value cos α or cos β of a unit vector connecting the calorific values of the natural gas from a location point $x_n$ to another location point $x_{n+1}$ may be the direction cosine value of the location point $x_n$. cos α may be the cosine value of the angle between the unit vector of the line connecting the location point $x_n$ to the location point $x_{n+1}$ and the axis x, and cos β may be the cosine value of the angle between the unit vector of the line connecting the location point $x_n$ to the location point $x_{n+1}$ and the axis y. The change of the calorific value of the natural gas at the target position in the natural gas transmission channel at different time points may be reflected by the direction cosine value.

In operation S208, a variable quantity of the direction cosine value at the each time point may be determined, and at least one time point may be determined as at least one cutpoint based on the variable quantity. The at least one cutpoint may be configured to determine a plurality of subareas of the area that the natural gas energy is to be measured. In some embodiments, the operation 604 may be performed by an area division module 604.

In some embodiments, each time point may correspond to a variable quantity of the direction cosine value. The variable quantity of the direction cosine value may be the variation of the direction cosine value between the location points. For example, the variable quantity of the direction cosine value corresponding to the location point $x_n$ may be the difference between the direction cosine value of the location point $x_n$ and the direction cosine value of the location point $x_{n-1}$, that is, cos $α_n$–cos $α_{n-1}$ or cos $β_n$–cos $β_{n-1}$. In some embodiments, the variable quantity of the direction cosine value may be determined by the processing device. In some embodiments, when the variable quantity the directional cosine value is greater than a preset threshold, the location point corresponding to the variable quantity of the directional cosine value may be used as the cutpoint.

The cutpoint may be location points used to determine the plurality of subareas of the area that the natural gas energy is to be measured.

In some embodiments, the cutpoint may reflect that the location point and the preceding and following location points may be discontinuous. In some embodiments, the area that the natural gas energy is to be measured may be divided based on the cutpoint. For example, the location point before the cutpoint and the location point after the cutpoint may be divided into different areas.

In operation S210, a calorific value distribution function of the calorific value of the natural gas corresponding to the each subarea may be determined based on the calorific value of the natural gas at the each time point in each subarea of the plurality of subareas. In some embodiments, the operation S210 may be performed by a function determination module 605.

The calorific value distribution function of the natural gas may be a function that reflects the distribution relationship between the time point in a subarea and the calorific value of the natural gas. For example, in some embodiments, the calorific value distribution function of the natural gas may be a constant (e.g., $f(x)=a$, and a is a constant), or a function $f(x)$ related to location x.

In some embodiments, for any subareas of the plurality of subareas, a linear function $f(x)$ (e.g., $f(x)=b\,x+c$) may be determined based on the calorific value of the natural gas corresponding to a first time point (corresponding to a first location point) and the calorific value of the natural gas corresponding to a last time point (corresponding to a last location point) in each subarea. In some embodiments, the linear function may be used as the calorific value distribution function of the subarea.

In some embodiments, the variation of the calorific value of the natural gas of a subarea may be a non-linear relationship and represented by a curve function $f(x)$. For example, when the calorific value distribution of the natural gas at different time points conforms to an exponential relationship, the calorific value distribution of the natural gas may be expressed by an exponential function; when the calorific value distribution of the natural gas at different time points conforms to a logarithmic relationship, the calorific value distribution of the natural gas may be expressed by a logarithmic function, or the like.

In some embodiments, for any subarea of the plurality of subareas, a fitting function $f(x)$ may be obtained based on a curve fitting method that is configured to fit the calorific value of the natural gas at the each time point in the each subarea, and the fitting method may be designated as the distribution function of the calorific value of the natural gas corresponding to the each subarea.

In some embodiments, the curve fitting method used to obtain the fitting function may include various existing curve fitting methods, such as the least square method.

In some embodiments, the calorific value distribution function of the natural gas may be determined by a first prediction model. For a detailed description of the first prediction model, refer to FIG. 3 and the related descriptions, which is not be repeated herein.

In some embodiments, different subareas may use different methods to determine the calorific value distribution functions of the natural gas of the subareas.

In operation S212, the natural gas energy of the each subarea of the plurality of subareas may be determined based on the calorific value distribution function of the natural gas corresponding to the each subarea. In some embodiments, the operation S212 may be performed by a subarea energy determination module 606.

The natural gas energy of the each subarea may be the energy generated through the combustion of the natural gas in a subarea.

In some embodiments, the natural gas energy of the each subarea may be determined by the calorific value distribution function of the natural gas. In some embodiments, the natural gas energy of the each subarea may be calculated by the following equation:

$$E = \int_0^{xk} f(x)dx \qquad (3)$$

wherein E refers to the natural gas energy of the each subarea, xk refers to the length of the location area in the length of the natural gas corresponding to the subarea k, k refers to the number of the subarea, and $f(x)$ refers to the calorific value distribution function of the natural gas corresponding to the subarea.

In operation S214, the natural gas energy of the area that the natural gas energy is to be measured may be determined based on the natural gas energy of the each subarea of the plurality of subareas. In some embodiments, the operation S214 may be performed by an area energy determination module 607.

The natural gas energy of the area that the natural gas energy is to be measured may be the sum of the energy generated by the complete combustion of the natural gas in each subarea of the area that the natural gas energy is to be measured.

Through the systems and methods for measuring natural gas energy according to some embodiments of the present disclosure, the area may be divided based on the changes of the natural gas components over a period of time, and the calorific value distribution of the natural gas may be obtained based on the changes of the natural gas components to obtain the natural gas energy of each subarea. The natural gas energy of the area that the natural gas energy is to be measured may be obtained based on the natural gas energy of the each subarea, so that the energy measurement of the area that the natural gas energy is to be measured may be closer to the actual situation of uneven distribution of the natural gas in the natural gas pipeline, and the measurement error can be reduced.

Figure 3:
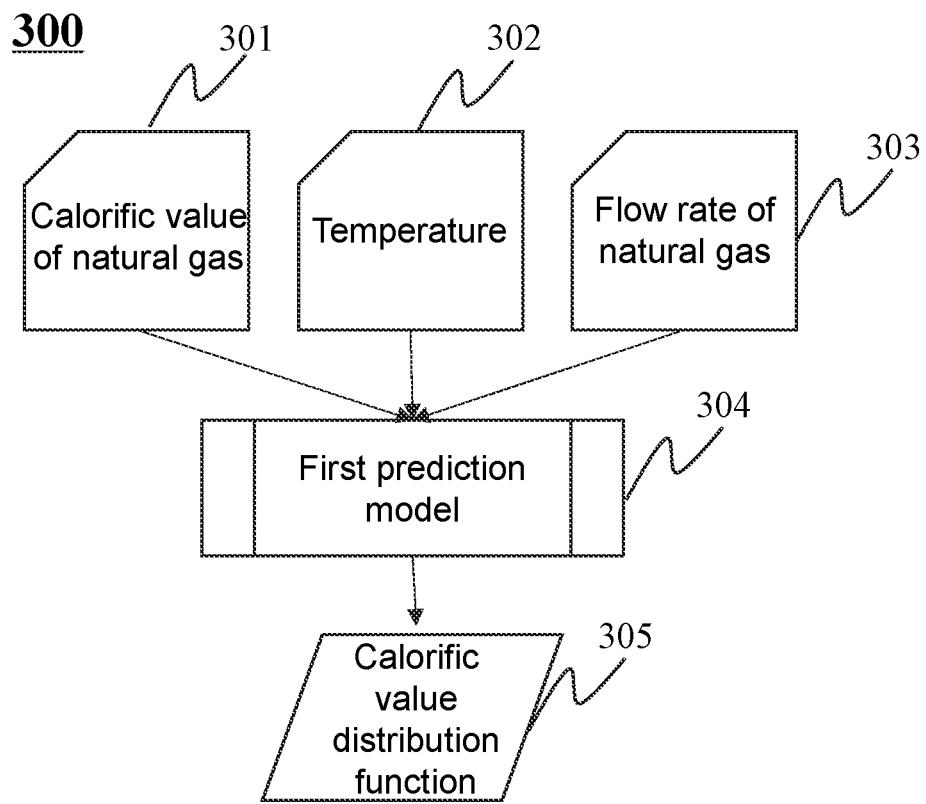
FIG. 3 is a schematic diagram of determining a calorific value distribution function of natural gas corresponding to each subarea based on a first prediction model according to some embodiments of the present disclosure.

FIG. 3 is a schematic diagram of determining a calorific value distribution function of the natural gas corresponding to each subarea based on a first prediction model according to some embodiments of the present disclosure.

As shown in FIG. 3, for any subarea in the plurality of subareas, a temperature 302 and a flow rate 303 of the natural gas at the each time point in the each subarea may be obtained, and the calorific value distribution function of the natural gas corresponding to the each subarea may be determined based on a first prediction model that is configured to process the calorific value of the natural gas 301, the temperature 302, and the flow rate of the natural gas 303 at the each time point in the each subarea.

The temperature at the each time point may be the temperature of the environment where the natural gas transmission channel is located at different time points. In some embodiments, the environmental temperature may fluctuate over time. In some embodiments, a temperature sensor may be used to record the gas temperature of the natural gas, or the temperature of a pipeline or a gas storage chamber containing the natural gas, so as to obtain the temperature at the each time point.

The flow rate of the natural gas at the each time point may be the gas flow rate at the target position in the natural gas transmission channel at different time points. In some embodiments, due to the influence of pressure or various factors, the flow rate of the natural gas flowing through the same target position at different time points may be different. In some embodiments, the flow rate of the natural gas may be determined by a ratio of the natural gas flow measured by a flowmeter to the measurement time, or directly determined by a measurement device of flow rate.

In some embodiments, the calorific value of the natural gas may be determined through the operation S202.

The first prediction model may be a machine learning model used to predict the calorific value distribution function of the natural gas. In some embodiments, the first prediction model may include a deep neural network, for example, various neural network models such as Deep Convolutional Network (DCN), Boltzmann Machine (BM), or the like.

In some embodiments, the input of the first prediction model may include the calorific value of the natural gas, the temperature, and the flow rate of the natural gas at the each time point in the subarea, and the output of the first prediction model may include the calorific value distribution function of the subarea.

Through the prediction model according to some embodiments of the present disclosure, various factors such as the temperature, the flow rate, or the like, are taken into consideration, and based on the machine learning model, the calorific value distribution function of the natural gas that is more in line with the actual natural gas transportation can be obtained.

In some embodiments, the first prediction model may be trained based on historical calorific value distribution data of the natural gas. In some embodiments, the historical calorific value distribution data of the natural gas of one or more sample areas that the natural gas energy is to be measured may be collected as input samples for the model, and the model may output a predicted value of the calorific value distribution function of the natural gas. In some embodiments, the actual combustion energy value of the natural gas of the sample area that the natural gas energy is to be measured may also be obtained. In some embodiments, a predicted energy value of the sample area that the natural gas energy is to be measured may be calculated based on the predicted value of the calorific value distribution function of the natural gas. For the relevant calculation method, refer to the description of FIG. 1. In some embodiments, a first loss function may be established based on the difference between the predicted energy value and the actual combustion energy value of the natural gas, and parameters of the first prediction model may be iteratively updated based on the loss function. In some embodiments, an optimization objective during training of the first prediction model may include minimizing the value of the first loss function. The model may be trained when the first loss function of the first prediction model satisfies a preset condition. The preset condition may be that the first loss function converges, the number of iterations reaches a threshold, or the loss function value reaches a minimum threshold, or the like.

In some embodiments, the historical calorific value distribution data of the natural gas of the sample area that the natural gas energy is to be measured and the actual combustion energy value of the natural gas may be acquired through the storage device or the network.

In some embodiments, the distribution of the natural gas components and the calorific value of the natural gas in FIG. 3 may be considered to be determined for the natural gas after the removal of impurities.

In some embodiments, the distribution of the natural gas components and the calorific value of the natural gas in FIG. 3 may be considered to be determined for the natural gas that the impurities are not removed. In some embodiments, FIG. 3 may also include the decontamination of the natural gas, and after the operation S210 in FIG. 3, one or more operations in a process 400 (e.g., operation S404, operation S406, operation S408) may also be included. For the detailed description of the decontamination and the process 400, refer to FIG. 4 and the related descriptions, which are not repeated herein.

Figure 4:
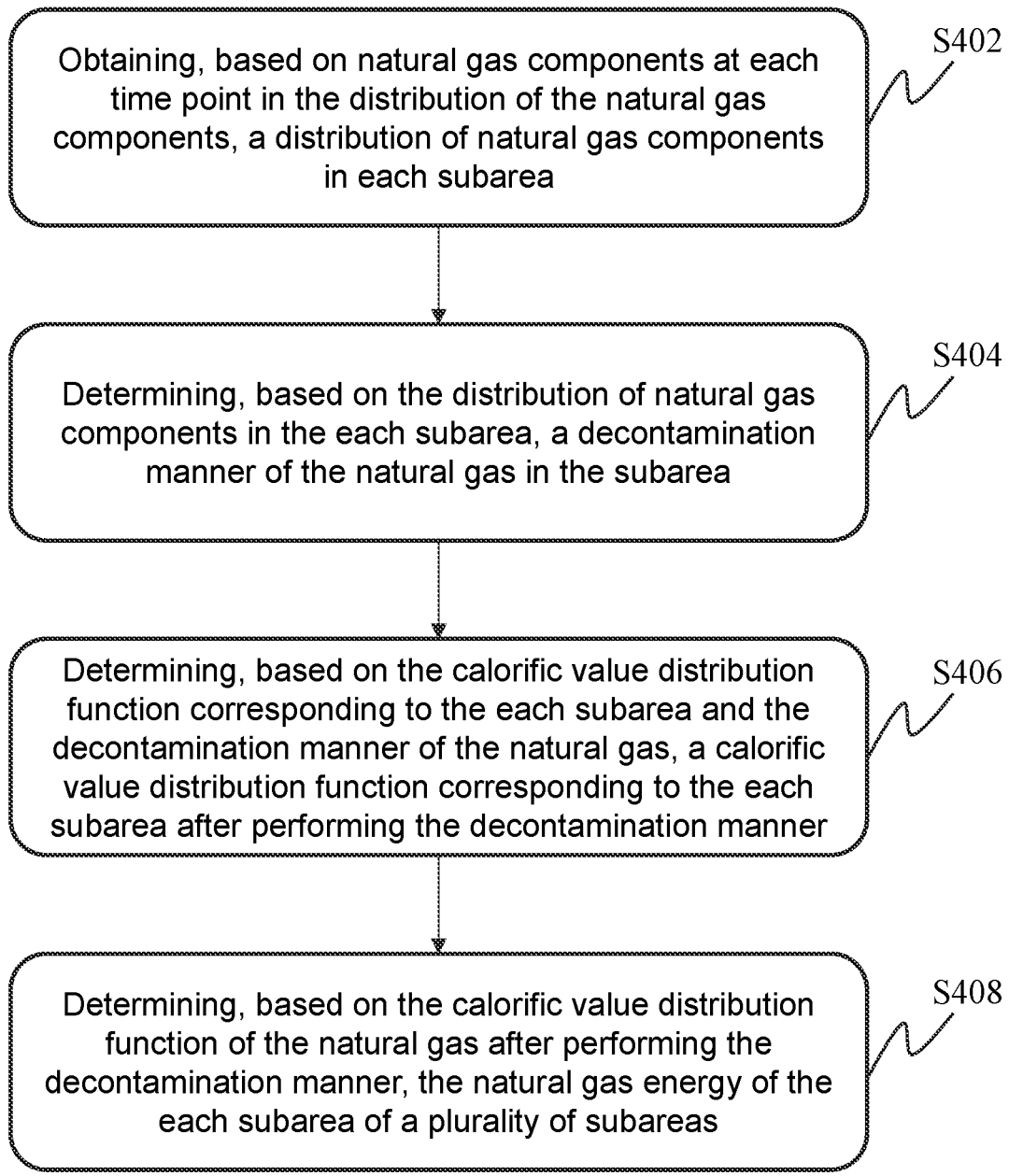
FIG. 4 is a schematic diagram of determining natural gas energy of a subarea based on a calorific value distribution function of natural gas after performing a decontamination manner according to some embodiments of the present disclosure.

FIG. 4 is a schematic diagram of determining natural gas energy of a subarea based on a calorific value distribution function of the natural gas after performing a decontamination manner according to some embodiments of the present disclosure. As shown in FIG. 4, the process 400 may include the following operations. In some embodiments, the process 400 may be performed by the processing device 120.

In operation S402, the distribution of the natural gas components in a subarea of a plurality of subareas may be obtained based on the natural gas components at the each time point in the distribution of the natural gas components. In some embodiments, the operation S402 may be performed by an subarea component distribution acquisition module 608.

For the method of obtaining the component distribution of the natural gas, refer to the related description of obtaining the distribution of the natural gas components in the area that the natural gas energy is to be measured in the operation S202, which is not be repeated herein.

The distribution of the natural gas components in the subarea may include the natural gas components at various time points in the subarea.

In operation S404, a decontamination manner of the natural gas corresponding to the each subarea may be determined based on the distribution of the natural gas components in the each subarea. The decontamination manner of the natural gas corresponding to a subarea may be configured to perform the decontamination manner of the natural gas on the subarea. In some embodiments, the operation S404 may be performed by a decontamination manner determination module 609.

The decontamination manner may be a technical manner to remove impurities such as water vapor impurities, hydrogen sulfide, carbon dioxide, or other acid gas impurities, solid impurities, liquid impurities, or other impurities in the natural gas components. For example, for water vapor impurities, the decontamination manner may include laying heating pipelines, heating water baths, installing dehydration devices, or the like. For solid impurities, the decontamination manner may include installing filters, or the like. For acid gas impurities such as hydrogen sulfide, carbon dioxide, or the like, the decontamination manner may include chemical absorption methods or the like.

In some embodiments, the decontamination manner may be determined based on the natural gas components.

In some embodiments, a component variation range of combustible gas or impurities of the each subarea may be determined based on the distribution of the natural gas components in the each subarea, and the decontamination manner of the natural gas corresponding to the each subarea may be determined based on the component variation range of the combustible gas or the impurities of the each subarea.

The variation range of the combustible gas or the impurities may be the variation range of a ratio of the combustible gas or the impurities in the natural gas. For example, the variation range of the combustible gas may be 85%-95%, and the variation range of the impurities may be 5%-15%. In some embodiments, the variation range of the impurities may include the variation range of the water vapor, the variation range of the acid gas, the variation range of the solid impurities, the variation range of the liquid impurities, or the like.

In some embodiments, when the variation range of impurities is within a preset variation interval of impurities, the decontamination manner corresponding to the preset interval may be designated as one of the final decontamination manners. For example, when the variation range of the acid gas such as hydrogen sulfide is greater than a preset variation interval of the acid gas impurities, a corresponding chemical absorption method may be used as one of the final decontamination manners.

In some embodiments, the decontamination manners corresponding to different subareas may be different.

Through the method for determining a decontamination manner according to some embodiments of the present disclosure, targeted, automatic, and accurate removal of impurities may be realized, unnecessary processes may be saved, and the possibility of introducing new impurities may be reduced.

In some embodiments, the method may further include performing the decontamination on the natural gas in the each subarea based on the decontamination manner corresponding to the each subarea.

In operation S406, a calorific value distribution function of the natural gas corresponding to the each subarea after performing the decontamination manner may be determined based on the calorific value distribution function of the natural gas corresponding to the each subarea and the decontamination manner of the natural gas. In some embodiments, the operation S406 may be performed by a function determination module 605.

In some embodiments, when the impurities are removed from the natural gas in the subarea, the distribution of the natural gas components in the subarea may change, and the corresponding calorific value distribution of the natural gas may also change accordingly.

In some embodiments, each calorific value distribution function of the natural gas and the calorific value distribution functions after performing the decontamination manner corresponding to various decontamination manners may be determined based on historical data of the natural gas, which may be used as templates. In some embodiments, the corresponding calorific value distribution function after performing the decontamination manner may be obtained by searching the templates according to the calorific value distribution function of the natural gas in the subarea and the decontamination manner corresponding to the subarea.

In some embodiments, the calorific value distribution function of the natural gas after performing the decontamination manner of the subarea may be determined based on the machine learning model. For the detailed description of the calorific value distribution function of the natural gas after performing the decontamination manner of the subarea determined based on the machine learning model, refer to FIG. 7 and the related description, which is not be repeated herein.

In operation S408, the natural gas energy of the each subarea in the plurality of subareas may be determined based on the calorific value distribution function of the natural gas after performing the decontamination manner. In some embodiments, the operation 606 may be performed by the subarea energy determination module 606.

In some embodiments, the natural gas energy of the subarea may be determined by an integrating calculation based on the calorific value distribution function of the natural gas after performing the decontamination manner. In some embodiments, the calculation equation of the natural gas energy of the subarea may be as follows:

$$E = \int_0^{x_k} f(x)' dx \qquad (4)$$

wherein E refers to the natural gas energy of the subarea, $x_k$ refers to a position in the length of the natural gas corresponding to the subarea, the area length k refers to the number corresponding to the subarea, and $f(x)'$ refers to the calorific value distribution function of the natural gas after performing the decontamination manner corresponding to the subarea. For the detailed description of the determination of the natural gas energy of the subarea, refer to the operation S212 and the related description, which may not be repeated herein.

Through the process according to some embodiments of the present disclosure, based on the variation range of the combustible gas or the impurities in each subarea, a corresponding decontamination manner may be selected to efficiently and accurately remove impurities, and automatic and precise removal of impurities for different types of impurities may be realized. Based on the component distribution after removing the impurities, the calorific value distribution function of the natural gas may be obtained to achieve a better function simulation.

It should be noted that the description about the process 400 is only for example and illustration, which does not limit the scope of the present disclosure. For those skilled in the art, various modifications and changes may be made to the process 400 under the guidance of the present disclosure. However, these corrections and changes may be still within the scope of the present disclosure. For example, the process 400 may also include a pre-processing process.

Figure 5:
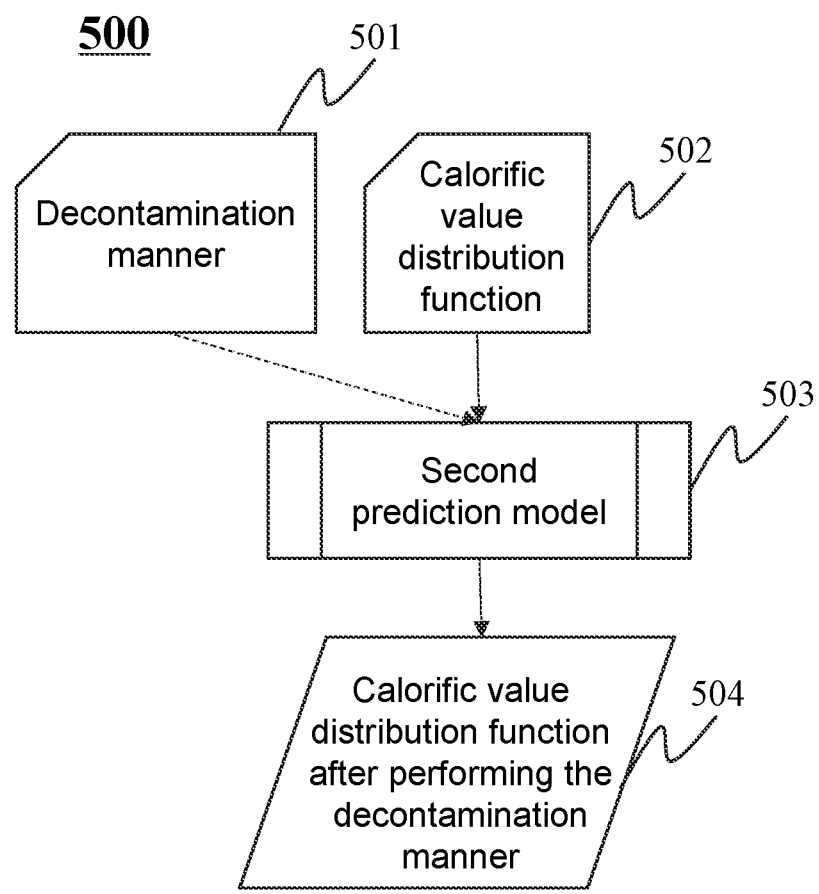
FIG. 5 is a schematic diagram of obtaining a calorific value distribution function of natural gas after performing a decontamination manner based on a second prediction model according to some embodiments of the present disclosure.

FIG. 5 is a schematic diagram of obtaining a calorific value distribution function of the natural gas after performing a decontamination manner based on a second prediction model according to some embodiments of the present disclosure.

As shown in FIG. 5, for any subarea in a plurality of subareas, a second prediction model 503 corresponding to the each subarea may be determined based on the decontamination manner 501 of the natural gas corresponding to the each subarea, and the calorific value distribution function of the natural gas 504 corresponding to the each subarea after performing the decontamination manner may be obtained based on the second prediction model that is configured to process the calorific value distribution function of the natural gas 502 corresponding to the each subarea.

The second prediction model may be a machine learning model for predicting the calorific value distribution function of the natural gas after performing the decontamination manner. In some embodiments, the second prediction model may be a convolutional neural network (CNN), a generative adversarial network (GAN), a generative adversarial model, DCN, BM, or the like, or other neural network models.

In some embodiments, the input of the second prediction model may be the calorific value distribution function of the natural gas, and the output of the second prediction model may be the calorific value distribution function after performing the decontamination manner. In some embodiments, the input of the second prediction model may also include a decontamination manner.

In some embodiments, the second prediction model may be trained based on historical data of the calorific value distribution function of the natural gas. In some embodiments, the historical calorific value distribution function of the natural gas and the historical calorific value distribution function of the natural gas after performing the decontamination manner obtained through various historical decontamination manner that removes the impurities may be used as the training samples. In some embodiments, the calorific value distribution function of the natural gas after performing the decontamination manner may be predicted by the second prediction model based on the historical calorific value distribution function of the natural gas and the historical decontamination manner. In some embodiments, a second loss function may be established based on the difference between the predicted calorific value distribution function of the natural gas after performing the decontamination manner and the historical calorific value distribution function of the natural gas after performing the decontamination manner, and parameters of the second prediction model may be iteratively updated based on the loss function. In some embodiments, a model optimization objective during training of the second prediction model may include minimizing the second loss function value. In some embodiments, model training may be completed when the second loss function of an initial second prediction model satisfies a preset condition. The preset condition may be that the loss function converges, the number of iterations reaches a threshold, the loss function value reaches a minimum threshold, or the like.

In some embodiments, a method for determining a label (the calorific value distribution function of the natural gas after performing the decontamination manner) trained by the second prediction model may include detecting the historical natural gas after performing the decontamination manner to determine the distribution of the natural gas components after performing the decontamination manner, and determining a corresponding historical calorific value distribution function of the natural gas based on the distribution of the natural gas components after performing the decontamination manner. For the method of detecting natural gas to determine the distribution of the natural gas components and determining the corresponding calorific value distribution function of the natural gas based on the distribution of natural gas components, refer to FIG. 2 and the related descriptions thereof. In some embodiments, the label may be obtained by manual marking or other feasible manners.

Through the second prediction model described according to some embodiments of the present disclosure, the calorific value distribution function of the natural gas may be further optimized based on the decontamination manner, so as to obtain a more realistic calorific value distribution of the natural gas in the pipeline after performing the decontamination manner.

Figure 6:
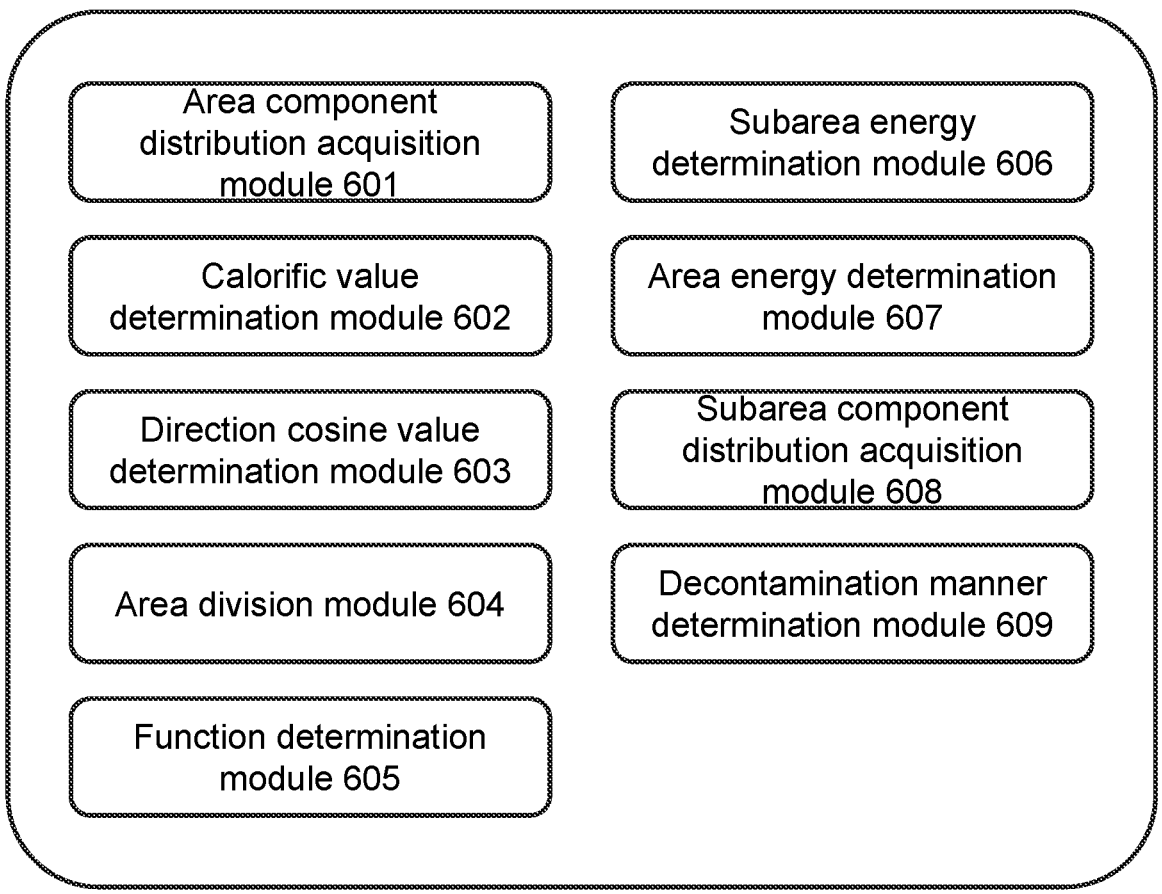
FIG. 6 is an exemplary block diagram of a system for measuring natural gas energy according to some embodiments of the present disclosure.

FIG. 6 is an exemplary block diagram of a system for measuring natural gas energy according to some embodiments of the present disclosure. As shown in FIG. 6, the module 600 may include an area component distribution acquisition module 601, a calorific value determination module 602, a direction cosine value determination module 603, an area division module 604, a function determination module 605, a subarea energy determination module 606, an area energy determination module 607, a subarea component distribution acquisition module 608, and a decontamination manner determination module 609. In some embodiments, the functions of the module 600 may be performed by the processing device 140, and the modules mentioned above may be a module in the processing device 140.

The area component distribution acquisition module 601 may be used to obtain the natural gas components at a target position in a natural gas transmission channel at each of a plurality of time points to obtain a distribution of the natural gas components in an area that the natural gas energy is to be measured.

The calorific value determination module 602 may be used to determine the calorific value of the natural gas at the each time point based on the natural gas components at the each time point of the distribution of the natural gas components at the each time point.

The direction cosine value determination module 603 may be used to determine the direction cosine value of the calorific value of the natural gas at the each time point.

The area division module 604 may be used to determine a variable quantity of the direction cosine value at the each time point, and determine, based on the variable quantity, at least one time point as at least one cutpoint. The at least one cutpoint may be configured to determine a plurality of subareas of the area that the natural gas energy is to be measured.

The function determination module 605 may be used to determine, based on the calorific value of the natural gas at the each time point in each subarea of the plurality of subareas, a calorific value distribution function of the calorific value of the natural gas corresponding to the each subarea. In some embodiments, the function determination module 605 may be further used to, for each of the plurality of subareas, determine, based on the calorific value of the natural gas corresponding to a first time point and the calorific value of the natural gas corresponding to a last time point in the each subarea, a linear function as the calorific value distribution function of the natural gas corresponding to the each subarea. In some embodiments, the function determination module 605 may be further used to, for each of the plurality of subareas, obtain a fitting function based on a curve fitting method that is configured to fit the calorific value of the natural gas at the each time point in the subarea, and designate the fitting method as the calorific value distribution function of the natural gas corresponding to the each subarea. In some embodiments, the function determination module 605 may be further used to, for each of the plurality of subareas, obtain a temperature and a flow rate of the natural gas at the each time point in the subarea, and determine, based on a first prediction model that is configured to process the calorific value of the natural gas, the temperature, and the flow rate of the natural gas at the each time point in the each subarea, the calorific value distribution function of the natural gas corresponding to the each subarea. In some embodiments, the function determination module 605 may be further used to determine, based on the calorific value distribution function of the natural gas corresponding to the each subarea and the decontamination manner of the natural gas, a calorific value distribution function of the natural gas corresponding to the each subarea after performing the decontamination manner. In some embodiments, the function determination module 605 may be further used to determine, based on the decontamination manner of the natural gas corresponding to the each subarea, a second prediction model corresponding to the each subarea, and obtain, based on the second prediction model that is configured to process the calorific value distribution function of the natural gas corresponding to the each subarea, the calorific value distribution function of the natural gas corresponding to the each subarea after performing the decontamination manner.

The subarea energy determination module 606 may be used to determine the natural gas energy of the each subarea of the plurality of subareas based on the calorific value distribution function of the natural gas corresponding to the each subarea. In some embodiments, the subarea energy determination module 606 may be further used to determine the natural gas energy of the each subarea of the plurality of subareas based on the calorific value distribution function of the natural gas after performing the decontamination manner.

The area energy determination module 607 may be used to determine the natural gas energy of the area that the natural gas energy is to be measured based on the natural gas energy of the each subarea of the plurality of subareas.

The subarea component distribution acquisition module 608 may be used to obtain the natural gas component distribution of the each subarea of the plurality of subareas based on the natural gas components at the each time point in the distribution of the natural gas components.

The decontamination manner determination module 609 may be used to determine the decontamination manner of the natural gas corresponding to the each subarea based on the natural gas component distribution of the each subarea of the plurality of subareas. The decontamination manner of the natural gas corresponding to a subarea may be configured to perform the decontamination manner on the natural gas of the subarea. In some embodiments, the decontamination manner determination module 609 may be further used to determine, based on the distribution of natural gas components in the subarea of the plurality of subareas, a component variation range of combustible gas or impurities of the each subarea, and determine, based on the component variation range of the combustible gas or the impurities of the each subarea, the decontamination manner of the natural gas corresponding to the each subarea.

Figure 9:
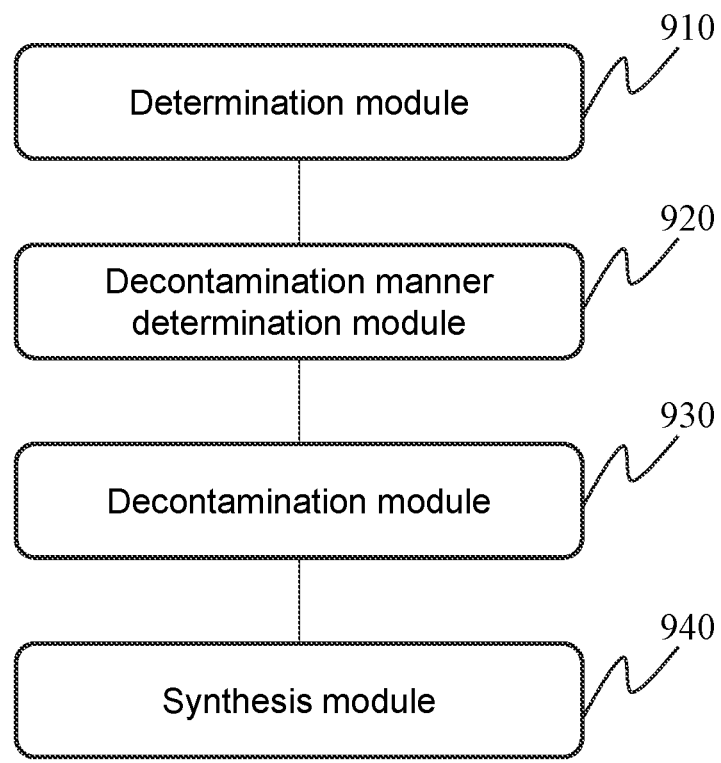
FIG. 9 is a block diagram of functional modules of an apparatus for obtaining measurement data of natural gas energy according to some embodiments of the present disclosure.

For more related descriptions about the modules, refer to the related descriptions of FIG. 9.

Figure 7:
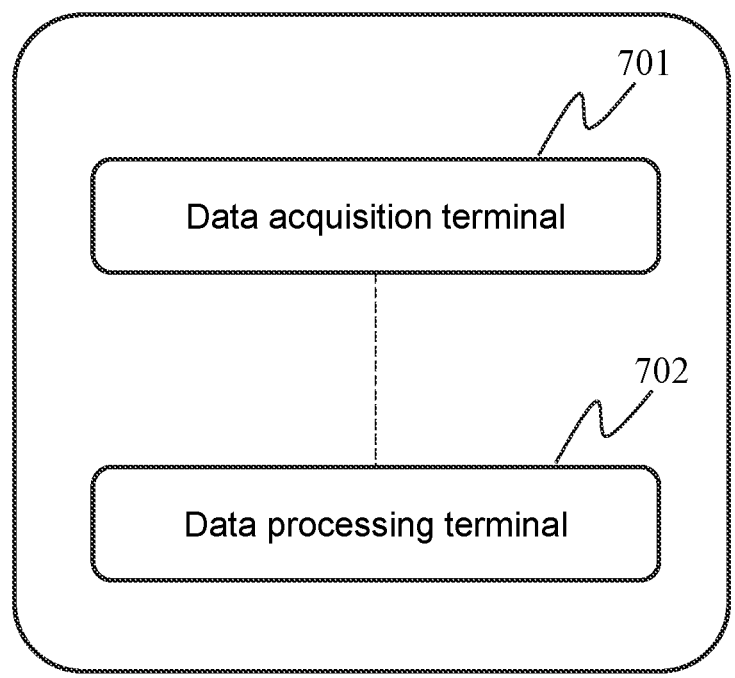
FIG. 7 is a schematic structural diagram of a system for obtaining measurement data of natural gas energy according to some embodiments of the present disclosure.

In order to facilitate the description of the method and apparatus for obtaining measurement data of natural gas energy, refer to FIG. 7, which provides a schematic diagram illustrating a communication architecture of a system 700 for obtaining measurement data of natural gas energy according to some embodiments of the present disclosure. The system 700 for obtaining measurement data of natural gas energy may include a data acquisition terminal 701 and a data processing terminal 702, and the data acquisition terminal 701 may be in communication with the data processing terminal 702.

In a specific embodiment, the data processing terminal 702 may be a desktop computer, a tablet computer, a notebook computer, a mobile phone, or other data collection terminals capable of data processing and data communication, which is not limited herein.

Figure 8:
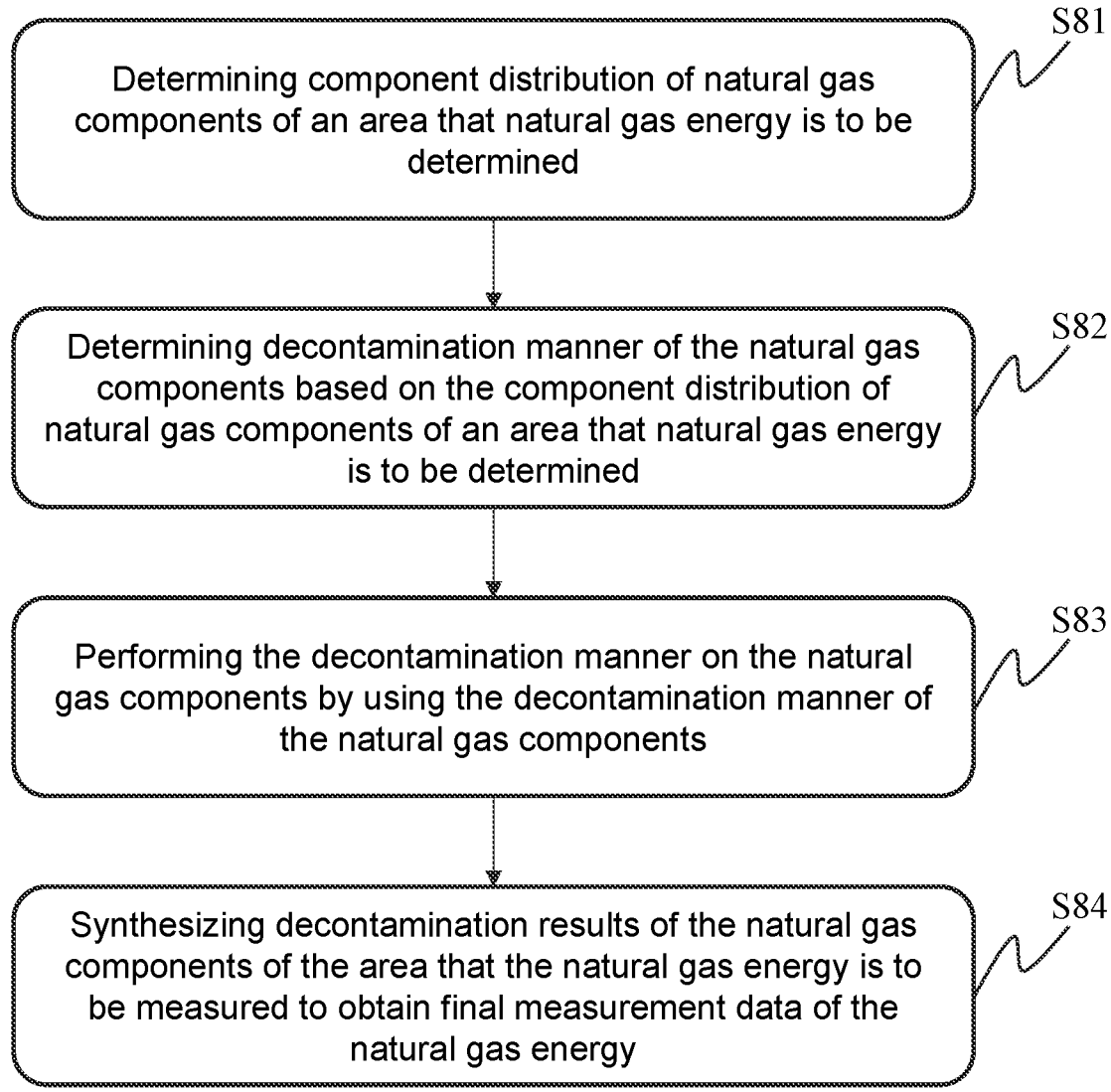
FIG. 8 is a flowchart of a method for obtaining measurement data of natural gas energy according to some embodiments of the present disclosure.

Regarding the above description to be processed, refer to FIG. 8, which is a schematic flowchart of a method for obtaining measurement data of natural gas energy according to some embodiments of the present disclosure. The method for obtaining measurement data of natural gas energy may be applied to be applied to the data acquisition terminal 701 in FIG. 7, and the method for obtaining measurement data of natural gas energy may specifically include the content described in the following operations S81 to S84.

In operation S81, the component distribution of the natural gas components of the area that the natural gas energy is to be measured may be determined.

In operation S82, the decontamination manner of the natural gas components may be determined based on the component distribution of the natural gas components of the area that the natural gas energy is to be measured.

In operation S83, the decontamination manner may be performed on the natural gas components through the decontamination manner of the natural gas components.

In operation S84, the decontamination results of the natural gas components of the area that the natural gas energy is to be measured may be synthesized to obtain final measurement data of the natural gas energy.

It should be understood that when the content described in the operations S81 and S84 is performed, by determining the component distribution of the natural gas components of the area that the natural gas energy is to be measured, the decontamination manner of the natural gas components may be determined according to the component distribution of the natural gas components of the area that the natural gas energy is to be measured, the decontamination manner of the natural gas components may be performed on the natural gas components to remove the impurities from the natural gas components, and the decontamination results of the natural gas components of the area that the natural gas energy is to be measured may be synthesized to obtain the final measurement data of the natural gas energy. Therefore, different decontamination manners are used to remove the impurities from the natural gas according to the type of natural gas components, which may effectively reduce statistical errors in energy measurement and effectively improve the accuracy of data energy measurement.

During the actual operation, the inventor found that when determining the component distribution of the natural gas components of the area that the natural gas energy is to be measured, there is a technical problem of uneven distribution, which is difficult to obtain an accurate distribution. In order to improve the technical problem mentioned above, the operation of determining the component distribution of the natural gas components of the area that the natural gas energy is to be measured described in the operation S81 may specifically include the content described in the following operations S811 and S812.

In operation S811, an edge detection may be performed on the area that the natural gas energy is to be measured to obtain an edge area.

In operation S812, the component distribution of the natural gas components of the area that the natural gas energy is to be measured may be determined based on an impurity value of the natural gas components in the edge area.

It should be understood that when the content described in the operations S811 and S812 is performed, when determining the component distribution of the natural gas components of the area that the natural gas energy is to be measured, the technical problem of uneven distribution may be avoided to obtain an accurate distribution.

During the actual operation, the inventor found that when the edge detection is performed on the area that the natural gas energy is to be measured, there may be a problem of detection error, which is difficult to obtain the edge area accurately. In order to improve the technical problems mentioned above, the operation of performing the edge detection on the area that the natural gas energy is to be measured to obtain the edge area described in the operation S811 may specifically include the content described in the following operations A1 to A3.

In operation A1, an energy operation may be performed on the area that the natural gas energy is to be measured with at least three energy measurement statistical models, respectively, to obtain at least three gradient cosine quantities of energy measurement.

In operation A2, gradient data of energy measurement of the area that the natural gas energy is to be measured may be determined based on the at least three gradient cosine quantities of energy measurement.

In operation A3, the gradient data of energy measurement may be classified and processed to obtain the edge area.

It should be understood that when performing the content described in the operations A1 to A3, the problem of detection errors may be avoided when the edge detection is performed on the area that the natural gas energy is to be measured, so that the edge area may be accurately obtained.

During the actual operation, the inventors found that it is difficult to accurately determine the component distribution of the natural gas components of the area that the natural gas energy is to be measured based on the impurity value of the edge area. In order to improve the technical problems mentioned above, the operation of determining the component distribution of the natural gas components of the area that the natural gas energy is to be measured based on the impurity value of the natural gas components of the edge area described in the operation S812 may specifically include the following operations Q1-Q3.

In operation Q1, edge natural gas components and real-time natural gas components may be determined based on the impurity value of each natural gas component of the edge area.

In operation Q2, if the impurity value of any adjacent natural gas component of the edge natural gas components is the same as the impurity value of the edge natural gas components, and the impurity value of any adjacent natural gas component of the adjacent natural gas component is the same as the impurity value of the adjacent natural gas component, the component distribution of the adjacent natural gas component and the adjacent natural gas component of the adjacent natural gas component may be determined to be the same as the component distribution of the edge natural gas component.

In operation Q3, if the amount of natural gas component in any component distribution is greater than or equal to a threshold value of the amount of natural gas components, it may be determined that the component distribution may be a continuous edge natural gas component; otherwise, it may be determined that the component distribution may be an independent edge natural gas component.

It should be understood that when performing the content described in the operations Q1-Q3, the technical problem of an error in the calculation of data may be avoided, so that the component distribution of natural gas components in the area that the natural gas energy is to be measured may be accurately determined.

In the actual operation process, the inventor found that when determining the component distribution of the natural gas components in the area that the natural gas energy is to be measured, there may be a problem of inaccurate calculation of the component distribution, which is difficult to accurately determine the decontamination manner of the natural gas components. In order to improve the technical problems, the operation of determining the decontamination manner of the natural gas components based on the component distribution of the natural gas components in the area that the natural gas energy is to be measured described in the operation S82 may specifically include the following operations S821 and S822.

In operation S821, the decontamination manner may be performed on the natural gas components of the continuous edge natural gas components of the area that the natural gas energy is to be measured to obtain an energy measurement result of the continuous edge natural gas components.

In operation S822, the decontamination manner may be performed on the area that the natural gas energy is to be measured, and the energy measurement result of the independent edge natural gas components or the real-time natural gas components may be extracted from the energy measurement result based on the position data of the independent edge natural gas components or the real-time natural gas components.

It should be understood that when the content described in the operations S821 and S822 is performed, and the component distribution of the natural gas components in the area that the natural gas energy is to be measured is determined, the problem of inaccurate calculation of the component distribution may be avoided, so that the decontamination manner of the natural gas components may be accurately determined.

In the actual operation process, the inventor found that when the decontamination manner is performed on the continuous edge natural gas components of the area that the natural gas energy is to be measured, there may be a technical problem of unclean decontamination, which is difficult to accurately obtain the measurement result of the continuous edge natural gas components. In order to improve the technical problems mentioned above, the operations described in the operation S821 may specifically include the following operation P1.

In operation P1, the same area as the area of the continuous edge natural gas components may be selected in a preset impurity filter template. An impurity filter weight of the preset impurity filter template may be adjusted based on the impurity value of the natural gas components in the area of the continuous edge natural gas components, and the adjusted impurity filter template may be used to filter the impurities in the area of the continuous edge natural gas components.

It should be understood that when the content described in the operation P1 is performed, and the decontamination manner is performed on the continuous edge natural gas components of the area that the natural gas energy is to be measured, the technical problem of unclean decontamination may be avoided, so that the energy measurement result of the continuous edge natural gas components may be accurately obtained.

In the actual operation process, the inventor found that when the decontamination manner is performed on the area that the natural gas energy is to be measured based on the position data of the independent edge natural gas components, there may be a problem of unreliable data processing, and the energy measurement results may not be reliable. The energy measurement result of the independent edge natural gas components may not be reliably extracted from the energy measurement results. In order to improve the technical problems mentioned above, the decontamination manner is performed on the area that the natural gas energy is to be measured as described in the operation S822, and the energy measurement result of the independent edge natural gas components may be extracted from the energy measurement results based on the position data of the independent edge natural gas components, which specifically includes the following operations K1 and K2.

In operation K1, a median filtering result of the area that the natural gas energy is to be measured may be obtained by performing the median filtering processing on the area that the natural gas energy is to be measured.

In operation K2, the corresponding median filtering result may be extracted from the median filtering result of the area that the natural gas energy is to be measured based on the position data of the independent edge natural gas components.

It should be understood that when the content described in the operations K1 and K2 is performed, and the decontamination manner is performed on the area that the natural gas energy is to be measured based on the position data of the independent edge natural gas components, the problem of unreliable data processing may be avoided, and the energy measurement result of the independent edge natural gas components may be reliably extracted from the energy measurement result.

In the actual operation process, the inventor found that the decontamination manner performed on the area that the natural gas energy is to be measured based on the position data of the real-time natural gas components may cause a technical problem that the position data of the real-time natural gas components is inaccurate, which is difficult to accurately extract the energy measurement result of the real-time natural gas components from the energy measurement results. In order to improve the technical problems mentioned above, the decontamination manner is performed on the area that the natural gas energy is to be measured as described in the operation S822, and the specific operations of extracting the energy measurement result of the independent edge natural gas components from the energy measurement results based on the position data of the independent edge natural gas components may specifically include the following operations K11 to K14.

In operation K11, the natural gas components of the area that the natural gas energy is to be measured may be compared with at least two similar block area templates, and a target similar block area template may be selected to be compared with the natural gas components from the at least two similar block area templates according to the comparison result.

In operation K12, the same real-time energy measurement area as the template area of the target similar block area may be determined in the area that the natural gas energy is to be measured.

In operation K13, a filtering weight of the area that the natural gas energy is to be measured may be determined based on the distance between the real-time energy measurement area and the target similar block area template.

In operation K14, the filtering process may be performed on the area that the natural gas energy is to be measured based on the determined filtering weight, and a corresponding filtering result may be extracted from the filtering results of the area that the natural gas energy is to be measured based on the position data of the real-time natural gas components.

It should be understood that, after performing the content described in the operations K11 to K14, the decontamination manner may be performed on the area that the natural gas energy is to be measured based on the position data of the real-time natural gas components, which avoids the technical problem of inaccurate position data of the real-time natural gas components, and the energy measurement result of the real-time natural gas components may be accurately extracted from the energy measurement results.

Based on the same inventive concept, a system for obtaining measurement data of natural gas energy may also be provided. The system may include a user platform, a service platform, a management platform, a sensor network platform, and a perception control platform. The user platform may be in communication with the service platform. The service platform may be in communication with the management platform. The management platform may be in communication with the sensor network platform. The sensor network platform may be in communication with the perception control platform. The user platform may further include a data acquisition terminal and a data processing terminal. The data acquisition terminal may be in communication with the data processing terminal, and the data processing terminal may be specifically configured to
- determine the component distribution of natural gas components of the area that the natural gas energy is to be measured;
- determine the decontamination manner of the natural gas components based on the component distribution of natural gas components of the area that the natural gas energy is to be measured;
- perform the decontamination manner on the natural gas components by using the decontamination manner of the natural gas components;
- synthesize the decontamination results of the natural gas components of the area that the natural gas energy is to be measured to obtain final measurement data of natural gas energy.

The data processing terminal may be further specifically configured to
- obtain an edge area by performing an edge detection on the area that the natural gas energy is to be measured;
- determine the component distribution of the natural gas components of the area that the natural gas energy is to be measured based on the impurity value of the natural gas components of the edge area.

The data processing terminal may be further specifically configured to obtain at least three gradient cosine quantities of energy measurement by performing energy calculation on the area that the natural gas energy is to be measured with at least three statistical models of energy measurement, respectively;
- determine gradient data of energy measurement of the area that the natural gas energy is to be measured based on the at least three gradient cosine quantities of energy measurement;
- classify the gradient data of energy measurement to obtain the edge area.

The data processing terminal may be further specifically configured to
- determine edge natural gas components and real-time natural gas components based on the impurity value of each natural gas component of edge area.

If the impurity value of any adjacent natural gas component of the edge natural gas components is the same as the impurity value of the edge natural gas components, and the impurity value of any adjacent natural gas component of the adjacent natural gas components is the same as the impurity value of the adjacent natural gas components, the component distribution of the adjacent natural gas components and the adjacent natural gas components of the adjacent natural gas components may be determined, which is the same as the component distribution of the edge natural gas components.

If the amount of natural gas components of any component distribution is greater than or equal to a threshold value of the amount of natural gas components, it may be determined that the component distribution is a continuous edge natural gas component; otherwise, the component distribution may be determined to be an independent edge natural gas component.

The data processing terminal may be further specifically configured to
- obtain an energy measurement result of the continuous edge natural gas components by performing the decontamination manner on the continuous edge natural gas component of the area that the natural gas energy is to be measured.
- perform the decontamination manner on the area that the natural gas energy is to be measured, and extract the energy measurement result of the independent edge natural gas component or the real-time natural gas component from the energy measurement results based on the position data of the independent edge natural gas components or the real-time natural gas components.

The data processing terminal may be further specifically configured to
- select the same area as the area of the continuous edge natural gas components in a preset impurity filtering template; adjust the impurity filtering weight of the preset impurity filtering template based on the impurity value of the natural gas components of the area of the continuous edge natural gas components, and use the adjusted impurity filtering template to filter impurities of the area of the continuous edge natural gas components.

The data processing terminal may be further specifically configured to
- perform median filtering process on the area that the natural gas energy is to be measured to obtain a median filtering result of the area that the natural gas energy is to be measured;
- extract a corresponding median filtering result from the median filtering result of the area that the natural gas energy is to be measured based on the position data of the independent edge natural gas components.

The data processing terminal may be further specifically configured to
- compare the natural gas components of the area that the natural gas energy is to be measured with at least two similar block area templates, and select a target similar block area template to be compared with the natural gas components from the at least two similar block area templates based on the comparison result;

determine the real-time energy measurement area the same as the target similar block area template of the area that the natural gas energy is to be measured;

determine the filtering weight of the area that the natural gas energy is to be measured based on the distance between the real-time energy measurement area and the target similar block area template;

perform the filtering process on the area that the natural gas energy is to be measured based on the determined filtering weight, and extract the corresponding impurity filtering result from the filtering results of the area that the natural gas energy is to be measured based on the position data of the real-time natural gas components.

Based on the same inventive concept mentioned above, refer to FIG. 9, a functional block diagram of an acquisition device 900 for obtaining measurement data of natural gas energy may also be provided. Detailed description of the acquisition device 900 for obtaining measurement data of natural gas energy may be as follows:

An acquisition device 900 for obtaining measurement data of natural gas energy may be applied to an image data processing terminal. The acquisition device 900 may comprise a determination module 910 configured to determine the component distribution of the natural gas components of the area that the natural gas energy is to be measured;

a determination module 920 of decontamination manner configured to determine the decontamination manner of the natural gas components based on the component distribution of the natural gas components of the area that the natural gas energy is to be measured;

a decontamination module 930 configured to perform the decontamination manner on the natural gas components by using the decontamination manner of the natural gas components;

a synthesis module 940 configured to synthesize the decontamination results of the natural gas components of the area that the natural gas energy is to be measured to obtain final measurement data of natural gas energy.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

In some embodiments, numbers describing the number of ingredients and attributes are used. It should be understood that such numbers used for the description of the embodiments use the modifier "about", "approximately", or "substantially" in some examples. Unless otherwise stated, "about", "approximately", or "substantially" indicates that the number is allowed to vary by ±20%. Correspondingly, in some embodiments, the numerical parameters used in the description and claims are approximate values, and the approximate values may be changed according to the required characteristics of individual embodiments. In some embodiments, the numerical parameters should consider the prescribed effective digits and adopt the method of general digit retention. Although the numerical ranges and parameters used to confirm the breadth of the range in some embodiments of the present disclosure are approximate values, in specific embodiments, settings of such numerical values are as accurate as possible within a feasible range.

For each patent, patent application, patent application publication, or other materials cited in the present disclosure, such as articles, books, specifications, publications, documents, or the like, the entire contents of which are hereby incorporated into the present disclosure as a reference. The application history documents that are inconsistent or conflict with the content of the present disclosure are excluded, and the documents that restrict the broadest scope of the claims of the present disclosure (currently or later attached to the present disclosure) are also excluded. It should be noted that if there is any inconsistency or conflict between the description, definition, and/or use of terms in the auxiliary materials of the present disclosure and the content of the present disclosure, the description, definition, and/or use of terms in the present disclosure is subject to the present disclosure. Finally, it should be understood that the embodiments described in the present disclosure are only used to illustrate the principles of the embodiments of the present disclosure. Other variations may also fall within the scope of the present disclosure. Therefore, as an example and not a limitation, alternative configurations of the embodiments of the present disclosure may be regarded as consistent with the teaching of the present disclosure.

Accordingly, the embodiments of the present disclosure are not limited to the embodiments introduced and described in the present disclosure explicitly.

What is claimed is:

1. A method for measuring energy of one or more natural gas components, implemented on a computing device including at least one temperature sensor, at least one measurement device, a storage device, and at least one processor, the method comprising:
obtaining, at each of a plurality of time points, the natural gas components at a target position in a natural gas transmission channel to obtain a distribution of the natural gas components in an area that the natural gas energy is to be measured;
determining, based on the natural gas components of the distribution of the natural gas components at the each time point, a calorific value of natural gas at the each time point;
determining a direction cosine value of the calorific value of the natural gas at the each time point;
determining a variable quantity of the direction cosine value at the each time point, and determining, based on the variable quantity, at least one time point as at least one cutpoint, the at least one cutpoint being configured to determine a plurality of subareas of the area that the natural gas energy is to be measured;
determining, based on the calorific value of the natural gas at the each time point in each subarea of the plurality of subareas, a calorific value distribution function corresponding to the each subarea; wherein the determining a calorific value distribution function corresponding to the each subarea includes:
for each of the plurality of subareas,
obtaining a temperature of the natural gas at the each time point in the subarea based on the at least one temperature sensor;
obtaining a flow rate of the natural gas at the each time point in the subarea based on the at least one measurement device; and
determining, based on a first prediction model that is configured to process the calorific value of the natural gas, and the temperature and the flow rate of the natural gas at the each time point in the subarea, the calorific value distribution function corresponding to the each subarea;
wherein the first prediction model is a neural network model; wherein
an input of the first prediction model includes the calorific value of the natural gas, and the temperature, and the flow rate of the natural gas at the each time point in the subarea, and an output of the first prediction model includes the calorific value distribution function corresponding to the each subarea;
the first prediction model is obtained by a first iterative training process, and
the first iterative training process includes:
collecting historical calorific value distribution data, historical temperature, and historical flow rate of the natural gas from one or more sample areas where the natural gas energy is to be measured as first training samples for an initial first prediction model,
inputting the first training samples into the initial first prediction model to output a predicted value of the calorific value distribution function of the natural gas;
obtaining actual combustion energy value of the natural gas from the one or more sample areas where the natural gas energy is to be measured;
calculating a predicted energy value of the natural gas from the one or more sample areas where the natural gas energy is to be measured based on the predicted value of the calorific value distribution function of the natural gas; and
establishing a first loss function based on a difference between the predicted energy value of the natural gas and the actual combustion energy value of the natural gas, and updating parameters of the initial first prediction model based on the first loss function and obtaining the first prediction model until the first loss function of the initial first prediction model satisfies a first preset condition;
wherein the first preset condition includes a convergence of the first loss function reaching a first threshold number of iterations or a value of the loss function falling below a minimum threshold;
determining, based on the calorific value distribution function corresponding to the each subarea, natural gas energy of the each subarea of the plurality of subareas; and
determining, based on the natural gas energy of the each subarea of the plurality of subareas, the natural gas energy of the area that the natural gas energy is to be measured.

2. The system of claim 1, wherein the determining, based on the calorific value of the natural gas at the each time point in each subarea of the plurality of subareas, a calorific value distribution function corresponding to the each subarea, includes:
for each of the plurality of subareas, determining, based on a calorific value of the natural gas corresponding to a first time point and a calorific value of the natural gas corresponding to a last time point in the subarea, a linear function as the calorific value distribution function of natural gas corresponding to the each subarea.

3. The method of claim 1, wherein the determining, based on the calorific value of natural gas at the each time point in each subarea of the plurality of subareas, a calorific value distribution function corresponding to the each subarea includes:
for each subarea of the plurality of subareas, obtaining a fitting function based on a curve-fitting manner that is configured to fit the calorific value of the natural gas at the each time point in the subarea, and designating the fitting function as the calorific value distribution function corresponding to the each subarea.

4. The method of claim 1, including:
obtaining, based on the natural gas components at the each time point in the distribution of the natural gas components, a distribution of natural gas components in the each subarea;
determining, based on the distribution of natural gas components in the each subarea, a decontamination manner of the natural gas corresponding to the each subarea, wherein the decontamination manner of the natural gas corresponding to a subarea is configured to perform the decontamination on the natural gas in the subarea;
determining, based on the calorific value distribution function corresponding to the each subarea and the decontamination manner of the natural gas, a calorific value distribution function of natural gas corresponding to the each subarea after performing the decontamination manner; and determining, based on the calorific value distribution function of the natural gas after performing the decontamination manner, the natural gas energy of the each subarea of the plurality of subareas.

5. The method of claim 4, wherein the determining, based on the distribution of natural gas components in the each subarea, a decontamination manner of the natural gas corresponding to the each subarea includes:

determining, based on the distribution of the natural gas components in the each subarea, a component variation range of combustible gas or impurities of the each subarea; and determining, based on the component variation range of the combustible gas or the impurities of the each subarea, the decontamination manner of the natural gas corresponding to the each subarea.

6. The method of claim 4, wherein the determining, based on the calorific value distribution function of natural gas corresponding to the each subarea and the decontamination manner of the natural gas, a distribution function of the calorific value of natural gas corresponding to the each subarea after performing the decontamination manner includes:

determining, based on the decontamination manner of the natural gas corresponding to the each subarea, a second prediction model corresponding to the each subarea; and obtaining, based on the second prediction model that is configured to process the calorific value distribution function of the natural gas corresponding to the each subarea, the calorific value distribution function of the natural gas corresponding to the each subarea after performing the decontamination manner;

wherein the second prediction model is a neural network model; wherein an input of the second prediction model includes the calorific value distribution function of the natural gas and the decontamination manner, and an output of the second prediction model includes the calorific value distribution function after performing the decontamination manner;

the second prediction model is obtained by a second iterative training process, and the second iterative training process includes: collecting historical calorific value distribution function of the natural gas and the historical calorific value distribution function of the natural gas after performing the decontamination manner obtained through various historical decontamination manner that removes the impurities as the second training samples;

establishing a second loss function based on a difference between a predicted calorific value distribution function of the natural gas after performing the decontamination manner and the historical calorific value distribution function of the natural gas after performing the decontamination manner, wherein the predicted calorific value distribution function of the natural gas after performing the decontamination manner is predicted by a initial second prediction model based on the historical calorific value distribution function of the natural gas and the historical decontamination manner; and updating parameters of the initial second prediction model based on the second loss function and obtaining the second prediction model until the second loss function of the initial second prediction model satisfies a second preset condition;

wherein the second preset condition includes a convergence of the second loss function reaching a second threshold number of iterations or a value of the loss function falling below a minimum threshold.

7. A system for measuring energy of natural gas components, comprising:

at least one temperature sensor;

at least one measurement device;

at least one storage device including a set of instructions; and at least one processor in communication with the at least one storage device, wherein when executing the set of instructions, the at least one processor is configured to cause the system to perform at least one operation comprising:

obtaining, at each of a plurality of time points, the natural gas components at a target position in a natural gas transmission channel to obtain a distribution of the natural gas components in an area that the natural gas energy is to be measured;

determining, based on the natural gas components of the distribution of the natural gas components at the each time point, a calorific value of natural gas at the each time point;

determining a direction cosine value of the calorific value of the natural gas at the each time point;

determining a variable quantity of the direction cosine value at the each time point, and determining, based on the variable quantity, at least one time point as at least one cutpoint, the at least one cutpoint being configured to determine a plurality of subareas of the area that the natural gas energy is to be measured;

determining, based on the calorific value of the natural gas at the each time point in each subarea of the plurality of subareas, a calorific value distribution function corresponding to the each subarea; wherein the determining a calorific value distribution function corresponding to the each subarea includes:

for each of the plurality of subareas, obtaining a temperature of the natural gas at the each time point in the subarea based on the at least one temperature sensor;

obtaining a flow rate of the natural gas at the each time point in the subarea based on the at least one measurement device; and determining, based on a first prediction model that is configured to process the calorific value of the natural gas, and the temperature and the flow rate of the natural gas at the each time point in the subarea, the calorific value distribution function corresponding to the each subarea;

wherein the first prediction model is a neural network model; wherein an input of the first prediction model includes the calorific value of the natural gas, and the temperature and the flow rate of the natural gas at the each time point in the subarea, and an output of the first prediction model includes the calorific value distribution function corresponding to the each subarea;

the first prediction model is obtained by a first iterative training process, and the first iterative training process includes:

collecting historical calorific value distribution data, historical temperature and historical flow rate of the natural gas from one or more sample areas where the natural gas energy is to be measured as first training samples for an initial first prediction model, inputting the first training samples into the initial first prediction model to output a predicted value of the calorific value distribution function of the natural gas;

obtaining actual combustion energy value of the natural gas from the one or more sample areas where the natural gas energy is to be measured;

calculating a predicted energy value of the natural gas from the one or more sample areas where the natural gas energy is to be measured based on the predicted value of the calorific value distribution function of the natural gas; and establishing a first loss function based on a difference between the predicted energy value of the natural gas and the actual combustion energy value of the natural gas, and updating parameters of the initial first prediction model based on the first loss function and obtaining the first prediction model until the first loss function of the initial first prediction model satisfies a first preset condition;

wherein the first preset condition includes a convergence of the first loss function reaching a first threshold number of iterations or a value of the loss function falling below a minimum threshold;

determining, based on the calorific value distribution function corresponding to the each subarea, natural gas energy of the each subarea of the plurality of subareas; and determining, based on the natural gas energy of the each subarea of the plurality of subareas, the natural gas energy of the area that the natural gas energy is to be measured.

8. The system of claim 7, wherein the at least one processor is further configured to cause the system to perform at least one operation comprising:

for each of the plurality of subareas, determining, based on a calorific value of the natural gas corresponding to a first time point and a calorific value of the natural gas corresponding to a last time point in the each subarea, a linear function as the calorific value distribution function of natural gas corresponding to the each subarea.

9. The system of claim 7, wherein the at least one processor is further configured to cause the system to perform at least one operation comprising:

for each of the plurality of subareas, obtaining a fitting function based on a curve-fitting manner that is configured to fit the calorific value of the natural gas at the each time point in the subarea, and designating the fitting function as the calorific value distribution function corresponding to the each subarea.

10. The system of claim 7, wherein the at least one processor is further configured to cause the system to perform at least one operation comprising:

obtaining, based on the natural gas components at the each time point in the distribution of the natural gas components, a distribution of natural gas components in the each subarea;

determining, based on the distribution of natural gas components in the each subarea, a decontamination manner of the natural gas corresponding to the each subarea, wherein the decontamination manner of the natural gas corresponding to a subarea is configured to perform the decontamination on the natural gas in the subarea;

determining, based on the calorific value distribution function corresponding to the each subarea and the decontamination manner of the natural gas, a calorific value distribution function of natural gas corresponding to the each subarea after performing the decontamination manner; and determining, based on the calorific value distribution function of the natural gas after performing the decontamination manner, the natural gas energy of the each subarea of the plurality of subareas.

11. The system of claim 10, wherein the at least one processor is further configured to cause the system to perform at least one operation comprising:

determining, based on the distribution of the natural gas components in the each subarea, a component variation range of combustible gas or impurities of the each subarea; and determining, based on the component variation range of the combustible gas or the impurities of the each subarea, the decontamination manner of the natural gas corresponding to the each subarea.

12. The system of claim 10, wherein the at least one processor is further configured to cause the system to perform at least one operation comprising:

determining, based on the decontamination manner of the natural gas corresponding to the each subarea, a second prediction model corresponding to the each subarea; and obtaining, based on the second prediction model that is configured to process the calorific value distribution function of the natural gas corresponding to the each subarea, the calorific value distribution function of the natural gas corresponding to the each subarea after performing the decontamination manner;

wherein the second prediction model is a neural network model; wherein an input of the second prediction model includes the calorific value distribution function of the natural gas and the decontamination manner, and an output of the second prediction model includes the calorific value distribution function after performing the decontamination manner;

the second prediction model is obtained by a second iterative training process, and the second iterative training process includes: collecting historical calorific value distribution function of the natural gas and the historical calorific value distribution function of the natural gas after performing the decontamination manner obtained through various historical decontamination manner that removes impurities as the second training samples;

establishing a second loss function based on a difference between a predicted calorific value distribution function of the natural gas after performing the decontamination manner and the historical calorific value distribution function of the natural gas after performing the decontamination manner, wherein the predicted calorific value distribution function of the natural gas after performing the decontamination manner is predicted by an initial second prediction model based on the historical calorific value distribution function of the natural gas and the historical decontamination manner; and updating parameters of the initial second prediction model based on the second loss function and obtaining the second prediction model until the second loss function of the initial second prediction model satisfies a second preset condition;

wherein the second preset condition includes a convergence of the second loss function reaching a second threshold number of iterations or a value of the loss function falling below a minimum threshold.

13. A non-transitory computer readable medium storing instructions, when executed by at least one processor, causing the at least one processor to implement a method comprising:

obtaining, at each of a plurality of time points, the natural gas components at a target position in a natural gas transmission channel to obtain a distribution of the natural gas components in an area that the natural gas energy is to be measured;

determining, based on the natural gas components of the distribution of the natural gas components at the each time point, a calorific value of natural gas at the each time point;

determining a direction cosine value of the calorific value of the natural gas at the each time point;

determining a variable quantity of the direction cosine value at the each time point, and determining, based on the variable quantity, at least one time point as at least one cutpoint, the at least one cutpoint being configured to determine a plurality of subareas of the area that the natural gas energy is to be measured;

determining, based on the calorific value of the natural gas at the each time point in each subarea of the plurality of subareas, a calorific value distribution function corresponding to the each subarea; wherein the determining a calorific value distribution function corresponding to the each subarea includes:

for each of the plurality of subareas, obtaining a temperature of the natural gas at the each time point in the subarea based on the at least one temperature sensor;

obtaining a flow rate of the natural gas at the each time point in the subarea based on the at least one measurement device; and determining, based on a first prediction model that is configured to process the calorific value of the natural gas, and the temperature and the flow rate of the natural gas at the each time point in the subarea, the calorific value distribution function corresponding to the each subarea;

wherein the first prediction model is a neural network model; wherein an input of the first prediction model includes the calorific value of the natural gas, and the temperature, and the flow rate of the natural gas at the each time point in the subarea, and an output of the first prediction model includes the calorific value distribution function corresponding to the each subarea;

the first prediction model is obtained by a first iterative training process, and the first iterative training process includes:

collecting historical calorific value distribution data, historical temperature, and historical flow rate of the natural gas from one or more sample areas where the natural gas energy is to be measured as first training samples for an initial first prediction model, inputting the first training samples into the initial first prediction model to output a predicted value of the calorific value distribution function of the natural gas;

obtaining actual combustion energy value of the natural gas from the one or more sample areas where the natural gas energy is to be measured;

calculating a predicted energy value of the natural gas from the one or more sample areas where the natural gas energy is to be measured based on the predicted value of the calorific value distribution function of the natural gas; and establishing a first loss function based on a difference between the predicted energy value of the natural gas and the actual combustion energy value of the natural gas, and updating parameters of the initial first prediction model based on the first loss function and obtaining the first prediction model until the first loss function of the initial first prediction model satisfies a first preset condition;

wherein the first preset condition includes a convergence of the first loss function reaching a first threshold number of iterations or a value of the loss function falling below a minimum threshold;

determining, based on the calorific value distribution function corresponding to the each subarea, natural gas energy of the each subarea of the plurality of subareas; and determining, based on the natural gas energy of the each subarea of the plurality of subareas, the natural gas energy of the area that the natural gas energy is to be measured.

* * * * *